(12) United States Patent
Bloomfield et al.

(10) Patent No.: US 7,902,375 B2
(45) Date of Patent: Mar. 8, 2011

(54) 5-PHENYL-4-METHYL-THIAZOL-2-YL-AMINE DERIVATIVES AS INHIBITORS OF PHOSPHATIDYLIN OSITOL 3 KINASE ENZYMES (PI13) FOR TREATMENT OF INFLAMMATORY DISEASES

(75) Inventors: Graham Charles Bloomfield, Horsham (GB); Ian Bruce, Horsham (GB); Judy Fox Hayler, Horsham (GB); Catherine Leblanc, Horsham (GB); Darren Mark Le Grand, Horsham (GB); Clive McCarthy, Basel (CH)

(73) Assignee: Novartis AG, Basel (CH)

( * ) Notice: Subject to any disclaimer, the term of this patent is extended or adjusted under 35 U.S.C. 154(b) by 410 days.

(21) Appl. No.: 10/568,053

(22) PCT Filed: Aug. 27, 2004

(86) PCT No.: PCT/EP2004/009586
§ 371 (c)(1),
(2), (4) Date: Jun. 18, 2008

(87) PCT Pub. No.: WO2005/021519
PCT Pub. Date: Mar. 10, 2005

(65) Prior Publication Data
US 2008/0280871 A1 Nov. 13, 2008

(30) Foreign Application Priority Data
Aug. 28, 2003 (GB) .................................. 0320197.7

(51) Int. Cl.
*A61K 31/427* (2006.01)
*C07D 417/12* (2006.01)

(52) U.S. Cl. ........................................ 548/196; 514/370

(58) Field of Classification Search .................... 548/196
See application file for complete search history.

(56) References Cited

FOREIGN PATENT DOCUMENTS

| WO | WO 01/17995 | 3/2001 |
| WO | WO 01/98270 | 12/2001 |
| WO | WO 02/10162 | 2/2002 |
| WO | WO-03/015778 A1 * | 2/2003 |
| WO | WO03/072557 | 9/2003 |

OTHER PUBLICATIONS

Alig et al., CA 131:116229, 1999.*

* cited by examiner

*Primary Examiner* — Laura L. Stockton
(74) *Attorney, Agent, or Firm* — Mark Milstead; Michael Smith

(57) ABSTRACT

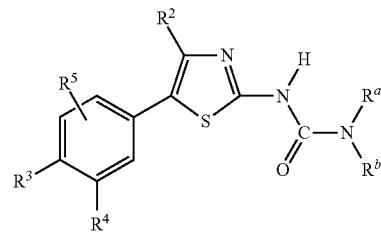

in free or salt form, wherein $R^a$, $R^b$, $R^2$, $R^3$, $R^4$ and $R^5$ have the meanings as indicated in the specification, are useful for treating conditions that are mediated by mediated by phosphatidylinositol 3-kinase. Pharmaceutical compositions that contain the compounds and a process for preparing the compounds are also described.

2 Claims, No Drawings

5-PHENYL-4-METHYL-THIAZOL-2-YL-AMINE DERIVATIVES AS INHIBITORS OF PHOSPHATIDYLIN OSITOL 3 KINASE ENZYMES (PI13) FOR TREATMENT OF INFLAMMATORY DISEASES

The present invention relates to organic compounds, their preparation and their use as pharmaceuticals.

In a first aspect, the present invention provides compounds of formula I

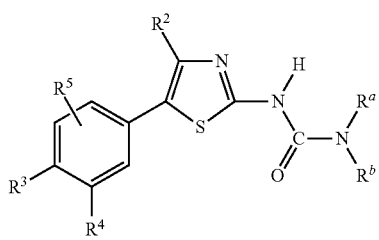

in free or salt form, wherein
$R^a$ is hydrogen or $C_1$-$C_4$-alkyl, $R^b$ is $C_1$-$C_8$-alkyl substituted by pyridyl, $R^3$ is $R^6$, and $R^4$ is fluoro or $C_1$-$C_8$-haloalkyl,
or $R^a$ is hydrogen or $C_1$-$C_4$-alkyl, $R^b$ is $C_1$-$C_8$-alkyl substituted by hydroxy or nitrile, $R^3$ is $R^6$, and $R^4$ is hydrogen or $C_1$-$C_8$-haloalkyl,
or $R^a$ is hydrogen or $C_1$-$C_4$-alkyl, $R^b$ is $C_1$-$C_8$-alkyl substituted by nitrile, $R^3$ is fluoro, and $R^4$ is $R^7$,
or $R^a$ is hydrogen or $C_1$-$C_4$-alkyl, $R^b$ is $C_1$-$C_8$-alkyl substituted by hydroxy, $R^3$ is fluoro, and $R^4$ is $R^7$,
or $R^a$ is hydrogen or $C_1$-$C_4$-alkyl, $R^b$ is $C_1$-$C_8$-alkyl substituted by di($C_1$-$C_8$-alkyl)amino, $R^3$ is $R^6$, and $R^4$ is $C_1$-$C_8$-haloalkyl,
or $R^a$ is hydrogen or $C_1$-$C_4$-alkyl, $R^b$ is $C_1$-$C_8$-alkyl substituted by —O—$C_1$-$C_8$-alkyl-OH, $R^3$ is $R^6$, and $R^4$ is fluoro or $C_1$-$C_8$-haloalkyl,
or $R^a$ is hydrogen or $C_1$-$C_4$-alkyl, $R^b$ is —CH($CH_3$)—CH—OH, $R^3$ is $R^6$, and $R^4$ is fluoro,
or $R^a$ is hydrogen or $C_1$-$C_4$-alkyl, $R^b$ is $C_1$-$C_8$-alkyl substituted by pyrrolidinyl substituted by $C_1$-$C_8$-alkyl, $R^3$ is $R^6$, and $R^4$ is $C_1$-$C_8$-haloalkyl,
or $R^a$ is hydrogen or $C_1$-$C_4$-alkyl, $R^b$ is $C_1$-$C_8$-alkyl substituted by oxazolyl substituted by $C_1$-$C_8$-alkyl, $R^3$ is $R^6$, and $R^4$ is nitrile or imidazolyl,
or $R^a$ is hydrogen or $C_1$-$C_4$-alkyl, $R^b$ is $C_1$-$C_8$-alkyl substituted by imidazolyl, $R^3$ is $R^6$, and $R^4$ is fluoro,
or $R^a$ is hydrogen or $C_1$-$C_4$-alkyl, $R^b$ is $C_1$-$C_8$-alkyl substituted by benzoimidazolyl, $R^3$ is $R^6$, and $R^4$ is fluoro,
or $R^a$ is hydrogen or $C_1$-$C_4$-alkyl, $R^b$ is $C_1$-$C_8$-alkyl substituted by isoxazolyl substituted by $C_1$-$C_8$-alkyl, $R^3$ is $R^6$, and $R^4$ is $R^7$,
or $R^a$ is hydrogen or $C_1$-$C_4$-alkyl, $R^b$ is $C_1$-$C_8$-alkyl substituted by pyrrolyl substituted by $C_1$-$C_8$-alkyl, $R^3$ is $R^6$, and $R^4$ is $R^7$,
or $R^a$ is hydrogen or $C_1$-$C_4$-alkyl, $R^b$ is $C_1$-$C_8$-alkyl substituted by pyrazolyl substituted by $C_1$-$C_8$-alkyl, $R^3$ is $R^6$, and $R^4$ is $R^7$,
or $R^a$ is hydrogen or $C_1$-$C_4$-alkyl, $R^b$ is $C_1$-$C_8$-alkyl substituted by —CO—O—$CH_3$, —CO—O-butyl, —CO-di($C_1$-$C_8$-alkyl)amino, —CO—$NH_2$, —NH—CO—$C_1$-$C_8$-alkyl, —$SO_2$-$C_1$-$C_8$-alkyl, —CO—NH—$R^c$ where $R^c$ is napthyl, or by —CO—NH—$C_1$-$C_8$-alkyl optionally substituted by di($C_1$-$C_8$-alkyl)-amino, $R^3$ is $R^6$, and $R^4$ is $R^7$,
or $R^a$ is hydrogen or $C_1$-$C_4$-alkyl, $R^b$ is —CH($CH_3$)—CO—NH—$C_1$-$C_8$-alkyl or —CH($CH_3$)—CO—O—$C_1$-$C_8$-alkyl, $R^3$ is $R^6$, and $R^4$ is $R^7$,
or $R^a$ is hydrogen or $C_1$-$C_4$-alkyl, $R^b$ is $C_1$-$C_8$-alkyl substituted by —CH(OH)—$CH_2$—OH, $R^3$ is $R^6$, and $R^4$ is $R^7$,
or $R^a$ is hydrogen or $C_1$-$C_4$-alkyl, $R^b$ is $C_1$-$C_8$-alkyl substituted by $C_1$-$C_8$-alkoxy, or by —S—$C_1$-$C_8$-alkyl, $R^3$ is $R^6$, and $R^4$ is $R^7$,
or $R^a$ is hydrogen or $C_1$-$C_4$-alkyl, $R^b$ is $C_1$-$C_8$-alkyl substituted by a 5- or 6-membered heterocyclic ring having one or more ring hetero atoms selected from the group consisting of oxygen, nitrogen and sulphur, that ring being substituted by oxo, $R^3$ is $R^6$, and $R^4$ is $R^7$,
or $R^a$ is hydrogen or $C_1$-$C_4$-alkyl, $R^b$ is $C_1$-$C_8$-alkyl substituted by a 5- or 6-membered heterocyclic ring having three or more ring hetero atoms selected from the group consisting of oxygen, nitrogen and sulphur, that ring being optionally substituted by $C_1$-$C_8$-alkyl, —$C_1$-$C_8$-alkyl-di($C_1$-$C_8$-alkyl)amino, or by $C_3$-$C_8$-cycloalkyl, $R^3$ is $R^6$, and $R^4$ is $R^7$,
or $R^a$ is hydrogen or $C_1$-$C_4$-alkyl, $R^b$ is $C_1$-$C_8$-alkyl substituted by oxazolyl substituted by $C_3$-$C_8$-alkyl, $R^3$ is $R^6$, and $R^4$ is $R^7$,
or $R^a$ is hydrogen or $C_1$-$C_4$-alkyl, $R^b$ is $C_1$-$C_8$-alkyl substituted by imidazolyl substituted by $C_1$-$C_8$-alkyl optionally substituted by hydroxy or $C_1$-$C_8$-alkoxy, $R^3$ is $R^6$, and $R^4$ is $R^7$,
or $R^a$ is hydrogen or $C_1$-$C_4$-alkyl, $R^b$ is $C_1$-$C_8$-alkyl substituted by —CO-Het where Het is a 5- or 6-membered heterocyclic ring having two or more ring hetero atoms selected from the group consisting of oxygen, nitrogen and sulphur, that ring being optionally substituted by $C_1$-$C_8$-alkyl, $R^3$ is $R^6$, and $R^4$ is $R^7$,
or $R^a$ is hydrogen or $C_1$-$C_4$-alllyl, $R^b$ is a 5- or 6-membered heterocyclic ring having one or more ring hetero atoms selected from the group consisting of oxygen, nitrogen and sulphur, that ring being substituted by oxo, $R^3$ is $R^6$, and $R^4$ is $R^7$,
or $R^a$ is hydrogen or $C_1$-$C_4$-alkyl, $R^b$ is an aza-bicyclo[3.2.1]oct-3-yl ring optionally substituted by $C_1$-$C_8$-alkyl, $R^3$ is $R^6$, and $R^4$ is $R^7$,
or $R^a$ and $R^b$ together form an azetidine ring substituted by $C_1$-$C_8$-alkoxycarbonyl or nitrile, $R^3$ is $R^6$, and $R^4$ is $R^7$,
or $R^a$ and $R^b$ together form a pyrrolidine ring substituted by —CO—$NH_2$ or nitrile, $R^3$ is $R^6$, and $R^4$ is $R^7$,
or $R^a$ and $R^b$ together form an imidazo-pyridine ring, $R^3$ is $R^6$, and $R^4$ is $R^7$;
$R^2$ is $C_1$-$C_4$-alkyl or halogen;
$R^5$ is hydrogen, halogen or $C_1$-$C_8$-alkyl;
$R^6$ is halo, —$SO_2$—$CH_3$, —$SO_2$—$CF_3$, carboxy, —CO—$NH_2$, —CO-di($C_1$-$C_8$-alkyl)amino, or a 5- or 6-membered heterocyclic ring having one or more ring hetero atoms selected from the group consisting of oxygen, nitrogen and sulphur, that ring being optionally substituted by halo, cyano, oxo, hydroxy, carboxy, nitro, $C_3$-$C_8$-cycloalkyl, $C_1$-$C_8$-alkylcarbonyl, $C_1$-$C_8$-alkoxy optionally substituted by aminocarbonyl, or $C_1$-$C_8$-alkyl optionally substituted by hydroxy, $C_1$-$C_8$-alkoxy, $C_1$-$C_8$-alkylamino or di($C_1$-$C_8$-alkyl)amino;
$R^7$ is hydrogen, halo, —$SO_2$—$CH_3$, nitrile, $C_1$-$C_8$-haloalkyl, imidazolyl, $C_1$-$C_8$-alkyl, —$NR^8R^9$, or —$SO_2$—$NR^8R^9$; and
$R^8$ and $R^9$ are independently hydrogen, amino, $C_1$-$C_8$-alkylamino, di($C_1$-$C_8$-alkyl)amino, or $C_1$-$C_8$-alkyl optionally substituted by hydroxy,
or $R^8$ and $R^9$ together form a 5- to 10-membered heterocyclic ring having one or more ring hetero atoms selected from the group consisting of oxygen, nitrogen and sulphur, that ring being optionally substituted by halo, cyano, oxo, hydroxy, carboxy, nitro, $C_3$-$C_8$-cycloalkyl, $C_1$-$C_8$-alkylcarbonyl, $C_1$-$C_8$-alkoxy optionally substituted by aminocarbonyl, or $C_1$-$C_8$-alkyl optionally substituted by hydroxy, $C_1$-$C_8$-alkoxy, $C_1$-$C_8$-alkylamino or di($C_1$-$C_8$-alkyl)amino.

Terms used in the specification have the following meanings:

"Substituted" as used herein means the group referred to is substituted at one or more positions by any one or any combination of the radicals listed thereafter.

"Optionally substituted" as used herein means the group referred to can be substituted at one or more positions by any one or any combination of the radicals listed thereafter.

"Halogen" or "halo" may be fluorine, chlorine, bromine or iodine. Preferably halogen or halo is fluorine or chlorine.

"$C_1$-$C_8$-alkyl" denotes straight chain or branched $C_1$-$C_8$-alkyl. Preferably, $C_1$-$C_8$-alkyl is $C_1$-$C_4$-alkyl.

"$C_1$-$C_8$-alkoxy" denotes straight chain or branched $C_1$-$C_8$-alkoxy. Preferably, $C_1$-$C_8$-alkoxy is $C_1$-$C_4$-alkoxy.

"$C_3$-$C_8$-cycloalkyl" denotes cycloalkyl having 3 to 8 ring carbon atoms, for example a monocyclic group such as a cyclopropyl, cyclobutyl, cyclopentyl, cyclohexyl, cycloheptyl or cyclooctyl, any of which can be substituted by one or more, usually one or two, $C_1$-$C_4$-alkyl groups, or a bicyclic group such as bicycloheptyl or bicyclooctyl. Preferably, "$C_3$-$C_8$-cycloalkyl" is $C_3$-$C_5$-cycloalkyl, especially cyclopropyl or cyclobutyl.

"$C_1$-$C_8$-haloalkyl" denotes $C_1$-$C_8$-alkyl as hereinbefore defined substituted by one or more halogen atoms as hereinbefore defined. Preferably, $C_1$-$C_8$-haloalkyl is $C_1$-$C_4$-alkyl substituted by one, two or three fluorine or chlorine atoms, especially —$CF_3$.

"Aminocarbonyl" as used herein denotes amino attached through the nitrogen atom to a carbonyl group.

"$C_1$-$C_8$-alkylcarbonyl" and "$C_1$-$C_8$-alkoxycarbonyl" denote $C_1$-$C_8$-alkyl and $C_1$-$C_8$-alkoxy respectively as hereinbefore defined attached by a carbon atom to a carbonyl group. Preferably, $C_1$-$C_8$-alkylcarbonyl and $C_1$-$C_8$-alkoxycarbonyl are respectively $C_1$-$C_4$-alkylcarbonyl and $C_1$-$C_4$-alkoxycarbonyl.

"$C_1$-$C_8$-alkylamino" and "di($C_1$-$C_8$-alkyl)amino" as used herein denote amino substituted respectively by one or two $C_1$-$C_8$-alkyl groups as hereinbefore defined, which may be the same or different. Preferably, $C_1$-$C_8$-alkylamino and di($C_1$-$C_8$-alkyl)amino are respectively $C_1$-$C_4$-alkylamino and di($C_1$-$C_4$-alkyl)amino.

"5- or 6-membered heterocyclic ring containing at least one ring heteroatom selected from the group consisting of nitrogen, oxygen and sulphur" as used herein may be, for example, furan, pyrrole, pyrrolidine, pyrazole, imidazole, triazole, isotriazole, tetrazole, thiadiazole, isothiazole, oxadiazole, pyridine, oxazole, isoxazole, pyrazine, pyridazine, pyrimidine, piperazine, morpholino, triazine, oxazine or thiazole. Preferred heterocyclic rings include piperazine, morpholino, imidazole, isotriazole, pyrazole, pyridine, furan, oxazole, isoxazole, oxadiazole and azetidine. The 5- or 6-membered heterocyclic ring can be unsubstituted or substituted. Preferred substituents include halo, cyano, oxo, hydroxy, carboxy, nitro, $C_3$-$C_8$-cycloalkyl, $C_1$-$C_8$-alkylcarbonyl, $C_1$-$C_8$-alkoxy optionally substituted by aminocarbonyl, and $C_1$-$C_8$-alkyl optionally substituted by hydroxy, $C_1$-$C_8$-alkoxy or di($C_1$-$C_8$-alkyl)amino. Especially preferred substituents include halo, oxo, $C_3$-$C_5$-cycloalkyl, and $C_1$-$C_4$-alkyl optionally substituted by hydroxy, $C_1$-$C_4$-alkoxy, $C_1$-$C_8$-alkylamino or di($C_1$-$C_4$-alkyl)amino.

"5- to 10-membered heterocyclic ring having one or more ring hetero atoms selected from the group consisting of oxygen, nitrogen and sulphur" as used herein may be, for example Preferred 5- to 10-membered heterocyclic rings include morpholino, piperazinyl and imidazolyl. The 5- to 10-membered heterocyclic ring can be unsubstituted or substituted. Preferred substituents include halo, cyano, oxo, hydroxy, carboxy, nitro, $C_3$-$C_8$-cycloalkyl, $C_1$-$C_8$-alkylcarbonyl, $C_1$-$C_8$-alkoxy optionally substituted by aminocarbonyl, or $C_1$-$C_8$-alkyl optionally substituted by hydroxy, $C_1$-$C_8$-alkoxy, $C_1$-$C_8$-alkylamino or di($C_1$-$C_8$-alkyl)amino. Especially preferred substituents include $C_1$-$C_4$-alkyl.

Throughout this specification and in the claims that follow, unless the context requires otherwise, the word "comprise", or variations such as "comprises" or "comprising", will be understood to imply the inclusion of a stated integer or step or group of integers or steps but not the exclusion of any other integer or step or group of integers or steps.

Preferred compounds of the present invention include compounds of formula I in free or salt form, wherein $R^a$ is hydrogen, $R^b$ is $C_1$-$C_8$-alkyl substituted by pyridyl, $R^3$ is $R^6$, and $R^4$ is fluoro or $C_1$-$C_8$-haloalkyl, or $R^a$ is hydrogen, $R^b$ is $C_1$-$C_8$-alkyl substituted by hydroxy or nitrile, $R^3$ is $R^6$, and $R^4$ is hydrogen or $C_1$-$C_8$-haloalkyl, or $R^a$ is hydrogen, $R^b$ is $C_1$-$C_8$-alkyl substituted by nitrile, $R^3$ is fluoro, and $R^4$ is $R^7$, or $R^a$ is hydrogen, $R^b$ is $C_1$-$C_8$-alkyl substituted by hydroxy, $R^3$ is fluoro, and $R^4$ is $R^7$, or $R^a$ is hydrogen, $R^b$ is $C_1$-$C_8$-alkyl substituted by di($C_1$-$C_8$-alkyl)amino, $R^3$ is $R^6$, and $R^4$ is $C_1$-$C_8$-haloalkyl, or $R^a$ is hydrogen, $R^b$ is $C_1$-$C_8$-alkyl substituted by —O—$C_1$-$C_8$-alkyl-OH, $R^3$ is $R^6$, and $R^4$ is fluoro or $C_1$-$C_8$-haloalkyl, or $R^a$ is hydrogen, $R^b$ is —CH($CH_3$)—$CH_2$—OH, $R^3$ is $R^6$, and $R^4$ is fluoro, or $R^a$ is hydrogen, $R^b$ is $C_1$-$C_8$-alkyl substituted by pyrrolidinyl substituted by $C_1$-$C_8$-alkyl, $R^3$ is $R^6$, and $R^4$ is $C_1$-$C_8$-haloalkyl, or $R^a$ is hydrogen, $R^b$ is $C_1$-$C_8$-alkyl substituted by oxazolyl substituted by $C_1$-$C_8$-alkyl, $R^3$ is $R^6$, and $R^4$ is nitrile or imidazolyl, or $R^a$ is hydrogen, $R^b$ is $C_1$-$C_8$-alkyl substituted by imidazolyl, $R^3$ is $R^6$, and $R^4$ is fluoro, or $R^a$ is hydrogen, $R^b$ is $C_1$-$C_8$-alkyl substituted by benzoimidazolyl, $R^3$ is $R^6$, and $R^4$ is fluoro, or $R^a$ is hydrogen, $R^b$ is $C_1$-$C_8$-alkyl substituted by isoxazolyl substituted by $C_1$-$C_8$-akyl, $R^3$ is $R^6$, and $R^4$ is $R^7$, or $R^a$ is hydrogen, $R^b$ is $C_1$-$C_8$-alkyl substituted by pyrrolyl substituted by $C_1$-$C_8$-alkyl, $R^3$ is $R^6$, and $R^4$ is $R^7$, or $R^a$ is hydrogen, $R^b$ is $C_1$-$C_8$-alkyl substituted by pyrazolyl substituted by $C_1$-$C_8$-alkyl, $R^3$ is $R^6$, and $R^4$ is $R^7$, or $R^a$ is hydrogen, $R^b$ is $C_1$-$C_8$-alkyl substituted by —CO—O—$CH_3$, —CO—O-butyl, —CO-di($C_1$-$C_8$-alkyl) amino, —CO—$NH_2$, —NH—CO—$C_1$-$C_8$-alkyl, —$SO_2$—$C_1$-$C_8$-alkyl, —CO—NH—$R^c$ where $R^c$ is napthyl, or by —CO—NH—$C_1$-$C_8$-alkyl optionally substituted by di($C_1$-$C_8$-alkyl)amino, $R^3$ is $R^6$, and $R^4$ is $R^7$, or $R^a$ is hydrogen, $R^b$ is —CH($CH_3$)—CO—NH—$C_1$-$C_8$-alkyl or —CH($CH_3$)—CO—O—$C_1$-$C_8$-alkyl, $R^3$ is $R^6$, and $R^4$ is $R^7$, or $R_a$ is hydrogen, $R^b$ is $C_1$-$C_8$-alkyl substituted by —CH(OH)—$CH_2$—OH, $R^3$ is $R^6$, and $R^4$ is $R^7$, or $R^a$ is hydrogen, $R^b$ is $C_1$-$C_8$-alkyl substituted by $C_1$-$C_8$-alkoxy, or by —S—$C_1$-$C_8$-alkyl, $R^3$ is $R^6$, and $R^4$ is $R^7$, or $R^a$ is hydrogen, $R^b$ is $C_1$-$C_8$-alkyl substituted by a 5- or 6-membered heterocyclic ring having one or more ring hetero atoms selected from the group consisting of oxygen, nitrogen and sulphur, that ring being substituted by oxo, $R^3$ is $R^6$, and $R^4$ is $R^7$, or $R^a$ is hydrogen, $R^b$ is $C_1$-$C_8$-alkyl substituted by a 5- or 6-membered heterocyclic ring having three or more ring hetero atoms selected from the group consisting of oxygen, nitrogen and sulphur, that ring being optionally substituted by $C_1$-$C_8$-alkyl, —$C_1$-$C_8$-alkyl-di($C_1$-$C_8$-alkyl) amino, or by $C_3$-$C_8$-cycloalkyl, $R^3$ is $R^6$, and $R^4$ is $R^7$, or $R^a$ is hydrogen, $R^b$ is $C_1$-$C_8$-alkyl substituted by oxazolyl substituted by $C_3$-$C_8$-alkyl, $R^3$ is $R^6$, and $R^4$ is $R^7$, or $R^a$ is hydrogen, $R^b$ is $C_1$-$C_8$-alkyl substituted by imidazolyl substituted by $C_1$-$C_8$-alkyl optionally substituted by hydroxy or $C_1$-$C_8$-alkoxy, $R^3$ is $R^6$, and $R^4$ is $R^7$, or $R^a$ is hydrogen, $R^b$ is $C_1$-$C_8$-alkyl substituted by —CO-Het where Het is a 5- or 6-membered heterocyclic ring having two or more ring hetero atoms selected from the group consisting of oxygen, nitrogen and sulphur, that ring being optionally substituted by $C_1$-$C_8$-alkyl, $R^3$ is $R^6$, and $R^4$ is $R^7$, or $R^a$ is hydrogen, $R^b$ is a 5- or 6-membered heterocyclic ring having one or more ring hetero atoms selected from the group consisting of oxygen, nitrogen and sulphur, that ring being substituted by oxo, $R^3$ is $R^6$, and $R^4$ is $R^7$, or $R^a$ is hydrogen, $R^b$ is an aza-bicyclo[3.2.1]oct-3-yl ring optionally substituted by $C_1$-$C_8$-alkyl, $R^3$ is $R^6$, and $R^4$ is $R^7$, or $R^a$ and $R^b$ together form an azetidine ring substituted by $C_1$-$C_8$-alkoxycarbonyl or nitrile, $R^3$ is $R^6$, and $R^4$ is $R^7$, or $R^a$ and $R^b$ together form a pyrrolidine ring substituted by —CO—$NH_2$ or nitrile, $R^3$ is $R^6$, and $R^4$ is $R^7$, or $R^a$ and $R^b$ together form an imidazo-pyridine ring, $R^3$ is $R^6$, and $R^4$ is $R^7$;

$R^2$ is $C_1$-$C_4$-alkyl or halogen;

$R^5$ is hydrogen;

$R^6$ is halo or —$SO_2$—$CH_3$; and $R^7$ is hydrogen, halo, —$SO_2$—$CH_3$, nitrile, $C_1$-$C_8$-haloalkyl or imidazolyl.

Especially preferred compounds of the present invention include compounds of formula I in free or salt form, wherein $R^a$ is hydrogen, $R^b$ is $C_1$-$C_4$-alkyl substituted by pyridyl, $R^3$ is $R^6$, and $R^4$ is fluoro or $C_1$-$C_4$-haloalkyl, or $R^a$ is hydrogen, $R^b$ is $C_1$-$C_4$-alkyl substituted by hydroxy or nitrile, $R^3$ is $R^6$, and $R^4$ is hydrogen or $C_1$-$C_4$-haloalkyl, or $R^a$ is hydrogen, $R^b$ is $C_1$-$C_4$-alkyl substituted by nitrile, $R^3$ is fluoro, and $R^4$ is $R^7$, or $R^a$ is hydrogen, $R^b$ is $C_1$-$C_4$-alkyl substituted by hydroxy, $R^3$ is fluoro, and $R^4$ is $R^7$, or $R^a$ is hydrogen, $R^b$ is $C_1$-$C_4$-alkyl substituted by di($C_1$-$C_4$-alkyl)amino, $R^3$ is $R^6$, and $R^4$ is $C_1$-$C_4$-haloalkyl, or $R^a$ is hydrogen, $R^b$ is $C_1$-$C_4$-alkyl substituted by —O—$C_1$-$C_4$-alkyl-OH, $R^3$ is $R^6$, and $R^4$ is fluoro or $C_1$-$C_4$-haloalkyl, or $R^a$ is hydrogen, $R^b$ is —CH($CH_3$)—$CH_2$—OH, $R^3$ is $R^6$, and $R^4$ is fluoro, or $R^a$ is hydrogen, $R^b$ is $C_1$-$C_4$-alkyl substituted by pyrrolidinyl substituted by $C_1$-$C_4$-alkyl, $R^3$ is $R^6$, and $R^4$ is $C_1$-$C_4$-haloalkyl, or $R^a$ is hydrogen, $R^b$ is $C_1$-$C_4$-alkyl substituted by oxazolyl substituted by $C_1$-$C_4$-alkyl, $R^3$ is $R^6$, and $R^4$ is nitrile or imidazolyl, or $R^a$ is hydrogen, $R^b$ is $C_1$-$C_4$-alkyl substituted by imidazolyl, $R^3$ is $R^6$, and $R^4$ is fluoro, or $R^a$ is hydrogen, $R^b$ is $C_1$-$C_4$-alkyl substituted by benzoimidazolyl, $R^3$ is $R^6$, and $R^4$ is fluoro, or $R^a$ is hydrogen, $R^b$ is $C_1$-$C_4$-alkyl substituted by isoxazolyl substituted by $C_1$-$C_4$-alkyl, $R^3$ is $R^6$, and $R^4$ is $R^7$, or $R^a$ is hydrogen, $R^b$ is $C_1$-$C_4$-alkyl substituted by pyrrolyl substituted by $C_1$-$C_4$-alkyl, $R^3$ is $R^6$, and $R^4$ is $R^7$, or $R^a$ is hydrogen, $R^b$ is $C_1$-$C_4$-alkyl substituted by pyrazolyl substituted by $C_1$-$C_4$-alkyl, $R^3$ is $R^6$, and $R^4$ is $R^7$, or $R^a$ is hydrogen, $R^b$ is $C_1$-$C_4$-alkyl substituted by —CO—O—$CH_3$, —CO—O-butyl, —CO-di($C_1$-$C_4$-alkyl)amino, —CO—$NH_2$, —NH—CO—$C_1$-$C_4$-alkyl, —$SO_2$-$C_1$-$C_4$-alkyl, —CO—NH—$R^c$ where $R^c$ is napthyl, or by —CO—NH—$C_1$-$C_4$-alkyl optionally substituted by di($C_1$-$C_4$-alkyl)amino, $R^3$ is $R^6$, and $R^4$ is $R^7$, or $R^a$ is hydrogen, $R^b$ is —CH($CH_3$)—CO—NH—$C_1$-$C_4$-alkyl or —CH($CH_3$)—CO—O—$C_1$-$C_4$-alkyl, $R^3$ is $R^6$, and $R^4$ is $R^7$, or $R^a$ is hydrogen, $R^b$ is $C_1$-$C_4$-alkyl substituted by —CH(OH)—$CH_2$—OH, $R^3$ is $R^6$, and $R^4$ is $R^7$, or $R^a$ is hydrogen, $R^b$ is $C_1$-$C_4$-alkyl substituted by $C_1$-$C_8$-alkoxy, or by —S—$C_1$-$C_4$-alkyl, $R^3$ is $R^6$, and $R^4$ is $R^7$, or $R^a$ is hydrogen, $R^b$ is $C_1$-$C_4$-alkyl substituted by a 5- or 6-membered heterocyclic ring having one or more ring hetero atoms selected from the group consisting of oxygen, nitrogen and sulphur, that ring being substituted by oxo, $R^3$ is $R^6$, and $R^4$ is $R^7$, or $R^a$ is hydrogen, $R^b$ is $C_1$-$C_4$-alkyl substituted by a 5- or 6-membered heterocyclic ring having three or more ring hetero atoms selected from the group consisting of oxygen, nitrogen and sulphur, that ring being optionally substituted by $C_1$-$C_8$-alkyl, —$C_1$-$C_8$-alkyl-di($C_1$-$C_4$-alkyl)-amino, or by $C_3$-$C_5$-cycloalkyl, $R^3$ is $R^6$, and $R^4$ is $R^7$, or $R^a$ is hydrogen, $R^b$ is $C_1$-$C_4$-alkyl substituted by oxazolyl substituted by $C_3$-$C_5$-alkyl, $R^3$ is $R^6$, and $R^4$ is $R^7$, or $R^a$ is hydrogen, $R^b$ is $C_1$-$C_4$-alkyl substituted by imidazolyl substituted by $C_1$-$C_4$-alkyl optionally substituted by hydroxy or $C_1$-$C_4$-alkoxy, $R^3$ is $R^6$, and $R^4$ is $R^7$, or $R^a$ is hydrogen, $R^b$ is $C_1$-$C_4$-alkyl substituted by —CO-Het where Het is a 5- or 6-membered heterocyclic ring having two or more ring hetero atoms selected from the group consisting of oxygen, nitrogen and sulphur, that ring being optionally substituted by $C_1$-$C_4$-alkyl, $R^3$ is $R^6$, and $R^4$ is $R^7$, or $R^a$ is hydrogen, $R^b$ is a 5- or 6-membered heterocyclic ring having one or more ring hetero atoms selected from the group consisting of oxygen, nitrogen and sulphur, that ring being substituted by oxo, $R^3$ is $R^6$, and $R^4$ is $R^7$, or $R^a$ is hydrogen, $R^b$ is an aza-bicyclo[3.2.1]oct-3-yl ring optionally substituted by $C_1$-$C_4$-alkyl, $R^3$ is $R^6$, and $R^4$ is $R^7$, or $R^a$ and $R^b$ together form an azetidine ring substituted by $C_1$-$C_4$-alkoxycarbonyl or nitrile, $R^3$ is $R^6$, and $R^4$ is $R^7$, or $R^a$ and $R^b$ together form a pyrrolidine ring substituted by —CO—$NH_2$ or nitrile, $R^3$ is $R^6$, and $R^4$ is $R^7$, or $R^a$ and $R^b$ together form an imidazo-pyridine ring, $R^3$ is $R^6$, and $R^4$ is $R^7$;

$R^2$ is $C_1$-$C_4$-alkyl or halogen;

$R^5$ is hydrogen;

$R^6$ is halo or —$SO_2$—$CH_3$; and $R^7$ is hydrogen, halo, —$SO_2$—$CH_3$, nitrile, $C_1$-$C_4$-haloalkyl or imidazolyl.

Many of the compounds represented by formula I are capable of forming acid addition salts, particularly pharmaceutically acceptable acid addition salts. Pharmaceutically acceptable acid addition salts of the compound of formula I include those of inorganic acids, for example, hydrohalic acids such as hydrofluoric acid, hydrochloric acid, hydrobromic acid or hydroiodic acid, nitric acid, sulfuric acid, phosphoric acid; and organic acids, for example aliphatic monocarboxylic acids such as formic acid, acetic acid, trifluoroacetic acid, propionic acid and butyric acid, aliphatic hydroxy acids such as lactic acid, citric acid, tartaric acid or malic acid, dicarboxylic acids such as maleic acid or succinic acid, aromatic carboxylic acids such as benzoic acid, p-chlorobenzoic acid, diphenylacetic acid or triphenylacetic acid, aromatic hydroxy acids such as o-hydroxybenzoic acid, p-hydroxybenzoic acid, 1-hydroxynaphthalene-2-carboxylic acid or 3-hydroxynaphthalene-2-carboxylic acid, and sulfonic acids such as methanesulfonic acid or benzenesulfonic acid. These salts may be prepared from compounds of formula I by known salt-forming procedures.

Compounds of formula I which contain acidic, e.g. carboxyl, groups, are also capable of forming salts with bases, in particular pharmaceutically acceptable bases such as those well known in the art; suitable such salts include metal salts, particularly alkali metal or alkaline earth metal salts such as sodium, potassium, magnesium or calcium salts, or salts with ammonia or pharmaceutically acceptable organic amines or heterocyclic bases such as ethanolamines, benzylamines or pyridine. These salts may be prepared from compounds of formula I by known salt-forming procedures.

Specific preferred compounds of formula I are described hereinafter in the Examples.

In a second aspect, the present invention provides a process for preparing a compound of formula I in free or salt form wherein $R^2$, $R^3$, $R^4$, $R^5$, $R^a$ and $R^b$ are as hereinbefore defined, which process comprises the steps of:

(i) (A) reacting a compound of formula II

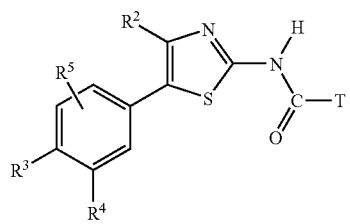

II wherein $R^2$, $R^3$, $R^4$ and $R^5$ are hereinbefore defined and T is a 5- or 6-membered heterocyclic ring having one or more ring hetero atoms selected from the group consisting of oxygen, nitrogen and sulphur, with a compound of formula III

III wherein $R^a$ and $R^b$ are hereinbefore defined;

(B) reacting compounds of formula IV

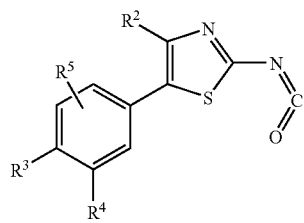

IV wherein $R^2$, $R^3$, $R^4$ and $R^5$ are hereinbefore defined with a compound of formula III wherein $R^a$ and $R^b$ are hereinbefore defined;

(C) for the preparation of compounds of formula I where $R^a$ is hydrogen and $R^2$, $R^3$, $R^4$, $R^5$ and $R^b$ are as hereinbefore defined, reacting a compound of formula V

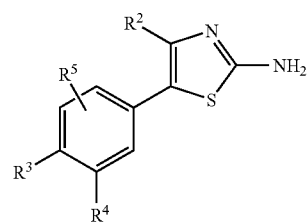

V wherein $R^2$, $R^3$, $R^4$ and $R^5$ are hereinbefore defined, with a compound of formula VI

VI wherein $R^b$ is as hereinbefore defined; or (D) for the preparation of compounds of formula I where $R^a$ is hydrogen, $R^b$ is $C_1$-$C_8$-alkyl substituted by imidazolyl substituted by $C_1$-$C_8$-alkyl optionally substituted by hydroxy or $C_1$-$C_8$-alkoxy and $R^2$, $R^3$, $R^4$ and $R^5$ are as hereinbefore defined, reacting a compound of formula V where $R^2$, $R^3$, $R^4$ and $R^5$ are hereinbefore defined, with a compound of formula VII

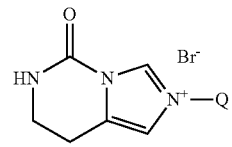

VII where Q is $C_1$-$C_8$-alkyl optionally substituted by hydroxy or $C_1$-$C_8$-alkoxy; and (ii) recovering the resultant compound of formula I in free or salt form.

Process variant (A) may be carried out using known procedures for reacting carbonyl di-heterocyclic intermediates (e.g. acylimidazolides when T is imidazole) with amines to form ureas, or analogously, e.g. as hereinafter described in the Examples. The reaction may be carried out in an organic solvent, e.g. dimethylformamide PMF) or dioxane, in the presence or absence of a base, for example triethylamine or sodium hydride. The reaction temperature may be from about 10° C. to about 100° C., but conveniently room temperature.

Process variant (B) mnay be carried out using known procedures for reacting isocyanates with amines, or analogously, e.g. as hereinafter described in the Examples. The reaction may be carried out in an organic solvent, e.g. dioxane or DMF. The reaction temperature may be an elevated temperature, for example from 50° C. to 100° C., but preferably about 80° C.

Process variants (C) may be carried out using known procedures for reacting isocyanates with amines, or analogously, e.g. as hereinafter described in the Examples. The reaction may be carried out in an organic solvent, e.g. dioxane or DMF, The reaction temperature may be an elevated temperature, for example from 50° C. to 100° C., but preferably about 80° C.

Process variant (D) may be carried out using known procedures for reacting 2-alkyl-5-oxo-5,6,7,8-tetrahydro-imidazo[1,5-c]pyrimidin-2-ium compounds with 2-amino-5-phenyl-thiazoles, or analogously, e.g. as hereinafter described in the Examples. The reaction may be carried out in an organic solvent, e.g. DMF, in the presence of a base, e.g. triethylamine. The reaction temperature may be 100-170° C., but conveniently about 120° C.

Compounds of formula II or formula IV may be prepared by reacting a compound of formula V wherein $R^2$, $R^3$, $R^4$ and $R^5$ are as hereinbefore defined with a compound of formula VIII

VIII wherein each T, which may be the same or different, is a 5- or 6-membered heterocyclic ring having one or more ring hetero atoms selected from the group consisting of oxygen, nitrogen and sulphur, using known procedures, or analogously, e.g. as described in the Examples. The compound of formula VIII is preferably 1,1'-carbonyldiimidazole (CDI). The reaction may be carried out in an organic solvent, e.g. dichloromethane (DCM). The reaction temperature may be from 20° C. to the reflux temperature of the solvent, but conveniently about 40° C.

Compounds of formula IV may also be prepared by reacting a compound of formula V wherein $R^2$, $R^3$, $R^4$ and $R^5$ are as hereinbefore defined, with phosgene, using known procedures, or analogously, e.g. as described in the Examples.

Compounds of formula III are commercially available or may be prepared by known methods, or analogously, e.g. as described in the Examples.

Compounds of formula V may be prepared by reacting a compound of formula IX

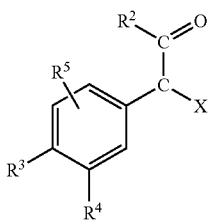
IX wherein $R^2$, $R^3$, $R^4$ and $R^5$ are as hereinbefore defined and X is a halogen, with thiourea, or analogously, using known procedures for preparing aminothiazoles. For example as described in the Examples below or as described in European patent specification EP 117082 A. The reaction may be carried out in an organic solvent, e.g. an alcohol such as ethanol. The reaction temperature may be from room temperature to the reflux temperature of the solvent, but conveniently from about 50° C. to about 70° C.

Compounds of formula V where $R^2$, $R^3$, $R^4$ and $R^5$ are as hereinbefore defined, may also be prepared by hydrolysing a compound of formula X

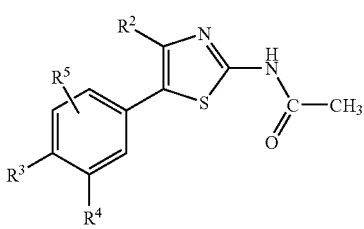
X where $R^2$, $R^3$, $R^4$ and $R^5$ are as hereinbefore defined, using aqueous sodium hydroxide or hydrochloric acid solution at temperatures of 50° C. to the reflux temperature of the solvent. A co-solvent, preferably ethanol may be added to aid solubility of the starting material.

Compounds of formula VI are commercially available or may be prepared by known methods, or analogously, e.g. as described in the Examples.

Compounds of formula VII may be prepared by known methods, for example as described in R. Jain and L. A. Cohen, *Tetrahedron* (1996), 52, p 5363-5370.

Compounds of formula VIII are commercially available or may be prepared by known methods, or analogously, e.g. as described in the Examples.

Compounds of formula IX are commercially available or may be prepared by reacting a compound of formula XI

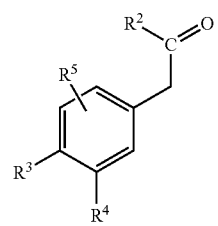
XI wherein $R^2$, $R^3$, $R^4$ and $R^5$ are as hereinbefore defined, with a halogenating agent, for example bromine, or analogously, e.g. as described in the Examples.

Compounds of formula X, where $R^3$ is $-SO_2CH_3$, $R^4$ is $NR^8R^9$ and $R^2$ and $R^5$ are as hereinbefore defined, may be prepared from compounds of formula IX where $R^3$ is $SO_2CH_3$, $R^4$ is a halogen, preferably fluorine, and $R^2$ and $R^5$ are as hereinbefore defined, using known procedures for reacting aryl halides, ortho to an electron withdrawing group, with primary or secondary amines, or analogously, e.g. as hereinafter described in the Examples. The reaction may be carried out either neat or in an organic solvent, e.g. dimethylsulphoxide. The reaction temperature may be from 100° C. to 170° C. but conveniently about 120° C. to 140° C.

Compounds of formula X, where $R^3$ is $-SO_2CH_3$, and $R^2$, $R^4$ and $R^5$ are as hereinbefore defined, may be prepared from compounds of formula X, where $R^3$ is $-SO_2Cl$ and $R^2$, $R^4$ and $R^5$ are as hereinbefore defined, using the procedure known in R W. Brown, *J. Org. Chem.*, (1991), 56, 4974 for converting sulfonyl halides to sulfones, or analogously, e.g. as hereinafter described in the Examples. The procedure may be carried out using an alkali metal sulphite, e.g. sodium sulphite, and an alkali metal bicarbonate, e.g. sodium bicarbonate, in water at a temperature from 20° C. to 100° C., but conveniently at about 75° C. The reaction with bromoacetic acid may be carried out at temperature from 50° C. to 150° C., but conveniently at about 100° C. An alkyl halide, e.g. iodomethane may be used in place of bromoacetic acid.

Compounds of formula X where $R^2$, $R^3$, $R^4$ and $R^5$ are as hereinbefore defined, may be prepared from compounds of formula IX, where $R^2$, $R^3$, $R^4$ and $R^5$ are as hereinbefore defined, as described analogously for the preparation of compounds of formula V, where $R^2$, $R^3$, $R^4$ and $R^5$ are as hereinbefore defined, but using N-acetyl thiourea instead of thiourea.

Compounds of formula X, where $R^3$ is —SO$_2$—Cl and $R^2$, $R^4$ and $R^5$ are as hereinbefore defined, may be prepared by reacting compounds of formula X, where $R^3$ is —NH$_2$ and $R^2$, $R^4$ and $R^5$ are as hereinbefore defined, with nitrous acid to give a diazo compound which is then reacted with sulphur dioxide in the presence of copper chloride, for example by the method described in E. E. Gilbert, *Synthesis* (1969),1-10, to give the corresponding sulfonyl chlorides.

Compounds of formula X, where $R^3$ is —NH$_2$ and $R^2$, $R^4$ and $R^5$ are as hereinbefore defined, may be prepared by reduction of compounds of formula X, where $R^3$ is —NO$_2$ and $R^2$, $R^4$ and $R^5$ are as hereinbefore defined using standard techniques known for the reduction of aromatic nitro compounds to anilines, for example catalytic hydrogenation using a transition metal catalyst, preferably palladium on carbon, in an organic solvent, e.g. ethyl acetate, under an atmosphere of hydrogen.

Compounds of formula X, where $R^3$ is —NO$_2$ and $R^2$, $R^4$ and $R^5$ are as hereinbefore defined are prepared by known procedures, for example as described in J. Liebscher, E. Mitzner, *Synthesis*, (1985), 4, 414-417.

Compounds of formula XI are commercially available or may be prepared from compounds of formula XII

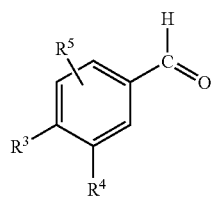

XII where $R^3$, $R^4$ and $R^5$ are as hereinbefore defined, using the method described in R. V. Heinzelman, *Org. Synth.* (1963), IV, 573, or analogously, e.g. as described in the Examples.

Compounds of formula XI where $R^3$ is halo, $R^4$ is —SO$_2$CH$_3$ and $R^2$ and $R^5$ are as hereinbefore defined may be prepared from a compound of formula XI where $R^3$ is halo, $R^4$ is hydrogen and $R^2$ and $R^5$ are as hereinbefore defined, using standard procedures e.g. treatment with chlorosulfonic acid followed by reduction with sodium sulfite using the procedure known in R. W. Brown, *J. Org. Chem.*, (1991), 56, 4974 for converting sulfonyl halides to sulfones, or analogously, e.g. as hereinafter described in the Examples. The reduction may be carried out with an alkali metal sulphite, e.g. sodium sulphite, and the alkali metal bicarbonate, e.g. sodium bicarbonate in water at a temperature from 20° C. to 100° C., but conveniently at about 75° C. followed by alkylation with methyl iodide.

Compounds of formula XII are commercially available or may be prepared by known methods, or analogously, e.g. as described in the Examples.

Compounds of formula XII where $R^3$ is —SO$_2$CH$_3$ and $R^4$ and $R^5$ are as hereinbefore defined may be prepared from compounds of formula XII where $R^3$ is halo and $R^4$ and $R^5$ are as hereinbefore defined, for example by the method described by A. Ulman and E. Urankar in *J. Org. Chem.*, (1989), 54, p 4691-4692, or analogously, e.g. as described in the Examples.

Compounds of formula I in free form may be converted into salt form, and vice versa, in a conventional manner. The compounds in free or salt form can be obtained in the form of hydrates or solvates containing a solvent used for crystallization. Compounds of formula I can be recovered from reaction mixtures and purified in a conventional manner. Isomers, such as enantiomers, may be obtained in a conventional manner, e.g. by fractional crystallization or asymmetric synthesis from correspondingly asymmetrically substituted, e.g. optically active, starting materials.

Compounds of formula I and their pharmaceutically acceptable salts, hereinafter referred to alternatively as agents of the invention, are useful as pharmaceuticals. In particular, they exhibit inhibition of phosphatidylinositol 3-kinase (Pi3 kinase) enzymes, especially the gamma isoform (p110γ), which are responsible for generating phosphorylated signalling products. The inhibitory properties of compounds of formula I may be demonstrated in the following test procedures:

Baculovirus expressing different fragments of PI3Kγ fused to GST have been previously described by Stoyanova, S., Bulgarelli-Leva, G., Kirsch, C., Hanck, T., Klinger, R., Wetzker, R., Wymann, M. P. (1997) Lipid- and protein kinase activities of G protein-coupled PI 3-kinase g: structure-activity analysis and interactions with wortmannin. *Biochem. J.*, 324:489. Residues 38-1102 of human PI3Kγ are subcloned into the BamH1 and EcoR1 sites of the transfer vector pAcG2T (Pharmingen) to create a GST-PI3Kγ lacking the first 37 residues of PI3Kγ. To express the recombinant protein, Sf9 (*Spodoptera frugiperda* 9) insect cells are routinely maintained at densities between 3×10⁵ and 3×10⁶ cells/ml in serum containing TNMFH medium (Sigma). Sf9 cells, at a density of 2×10⁶ are infected with human GST-PI3KγΔ34 baculovirus at a multiplicity of infection (m.o.i.) of 1 for 72 hours. The infected cells are harvested by centrifugation at 1400 g for 4 minutes at 4° C. and the cell pellets are frozen at −80° C. Both Sf9 and Sf21 cells work equally well. Sf9 cells (1×10⁹) are resuspended in 100 ml cold (4° C.) lysis buffer (50 mM Tris-HCl pH 7.5, 1% Triton X-100, 150 mM NaCl, 1 mM NaF, 2 mM DTT and protease inhibitors. Cells are incubated on ice for 30 minutes then centrifuged at 15000 g for 20 minutes at 4° C. Purification of the supernatant sample is carried out at 4° C. by affinity chromatography using SEPHAROSE™ agarose gel beads coupled to glutathione (from Amersham Pharmacia Biotech). A cell lysate/GST resin ratio of 50:1 is used. The GST resin is firstly pre-rinsed to remove ethanol preservative and then equilibrated with lysis buffer. Cell lysate (supernatant) is added (usually as 50 ml lysate to 1 ml GST resin in 50 ml tubes) and gently rotated on a mixer at 4° C. for 2-3 hours. The unbound flow through sample is collected by centrifugation at 1000 g for 5 minutes at 4° C. using a DENLEY™ centrifuge. The 1 ml GST resin containing bound material is transferred to a 15 ml FALCON™ centrifuge tube for subsequent washing and elution steps. Firstly a series of 3 cycles of washings (mixing by gentle inversion) is performed with 15 ml ice cold wash Buffer A (50 mM Tris-HCl pH 7.5, 1% Triton X-100, 2 mM DTT) interspersed with centrifugation at 1000 g for 5 minutes at 4° C. A final single wash step is performed with 15 ml ice cold wash Buffer B (50 mM Tris-HCl pH 7.5, 2 mM DTT) and then centrifuged at 1000 g for 5 minutes at 4° C. The washed GST resin is finally eluted with 4 cycles of 1 ml ice cold elution buffer (50 mM Tris-HCl pH 7.5, 10 mM reduced glutathione, 2 mM DTT, 150 mM NaCl, 1 mM NaF, 50% ethylene glycol and protease inhibitors) interspersed with centrifugation at 1000 g for 5 minutes at 4° C. Samples are aliquoted and stored at −20° C.

An in vitro kinase assay was established that measures the transfer of the terminal phosphate of adenosine triphosphate to phosphatidylinositol. The kinase reaction is performed in a white 96 well microtitre plate as a Scintillation Proximiy Assay. Each well contains 10 μl test compound in 5% dimethylsulphoxide and 20 μl assay mix (40 mM Tris, 200 mM NaCl, 2 mM ethyleneglycol-aminoethyl-tetraacetic acid (EGTA), 15 µg/ml phosphatidylinositol, 12.5 µM adenosine triphosphate (ATP), 25 mM MgCl$_2$, 0.1 µCi [$^{33}$P]ATP). The reaction is started by the addition of 20 µl of enzyme mix (40 mM Tris, 200 mM NaCl, 2 mM EGTA containing recombinant GST-p110γ). The plate is incubated at room temperature for 60 minutes and the reaction terminated by the adding 150 µl of WGA-bead stop solution (40 mM Tris, 200 mM NaCl, 2 mM EGTA, 1.3 mM ethylene diamine tetraacetic acid (EDTA), 2.6 µM ATP and 0.5 mg of Wheat Germ Agglutinin-SPA beads (Amersham Biosciences) to each well. The plate is sealed, incubated at room temperature for 60 minutes, centrifuged at 1200 rpm and then counted for 1 minute using a scintillation counter. Total activity is determined by adding 10 µl of 5% dimethylsulphoxide (DMSO) and non-specific activity is determined by adding 10 µl 50 mM EDTA in place of the test compound.

Compounds of the Examples hereinbelow have IC$_{50}$ (γ) values below 0.5 µM in the aforementioned assay or demonstrate selectivity with respect to the γ, α, δ or β isoform as determined by a corresponding assay. For example the compounds of Examples 11, 19, 29, 40, 66, 75, 89, 96, 98 and 116 have IC$_{50}$ (γ,α,δ) µM values of (0.016,3.018,0.626), (0.012, 0.009,0.028), (0.047,0.035,0.180), (0.213,2.059,2.616), (0.177,0.218,0.637), (0.195,0.190,–), (0.074,0.839,3.792), (0.038,0.934,2.150), (0.044,1.500,0.420) and (0.032,0.156, 0.170) respectively, and compounds of Examples 121, 124, 131, 138, 145 and 150 have IC$_{50}$ (γ) µM values of 0.019, 0.007, 0.017, 0.018, 0.017 and 0.056 respectively.

Having regard to their inhibition of phosphatidylinositol 3-kinase enzymes, compounds of formula I in free or pharmaceutically acceptable salt form, hereinafter alternately referred to as "agents of the invention", are useful in the treatment of conditions which are mediated by the activation of the Pi3 kinase enzymes, particularly inflammatory or allergic conditions. Treatment in accordance with the invention may be symptomatic or prophylactic.

Accordingly, agents of the invention are useful in the treatment of inflammatory or obstructive airways diseases, resulting, for example, in reduction of tissue damage, airways inflammation, bronchial hyper-reactivity, remodelling or disease progression. Inflammatory or obstructive airways diseases to which the present invention is applicable include asthma of whatever type or genesis including both intrinsic (non-allergic) asthma and extrinsic (allergic) asthma, mild asthma, moderate asthma, severe asthma, bronchitic asthma, exercise-induced asthma, occupational asthma and asthma induced following bacterial infection. Treatment of asthma is also to be understood as embracing treatment of subjects, e.g. of less than 4 or 5 years of age, exhibiting wheezing symptoms and diagnosed or diagnosable as "wheezy infants", an established patient category of major medical concern and now often identified as incipient or early-phase asthnatics. (For convenience this particular asthmatic condition is referred to as "wheezy-infant syndrome".)

Prophylactic efficacy in the treatment of asthma will be evidenced by reduced frequency or severity of symptomatic attack, e.g. of acute asthmatic or bronchoconstrictor attack, improvement in lung function or improved airways hyper-reactivity. It may further be evidenced by reduced requirement for other, symptomatic therapy, i.e. therapy for or intended to restrict or abort symptomatic attack when it occurs, for example anti-inflammatory (e.g. corticosteroid) or bronchodilatory. Prophylactic benefit in asthma may in particular be apparent in subjects prone to "morning dipping". "Morning dipping" is a recognised asthmatic syndrome, common to a substantial percentage of asthmatics and characterised by asthma attack, e.g. between the hours of about 4 to 6 am, i.e. at a time normally substantially distant form any previously administered symptomatic asthma therapy.

Other inflammatory or obstructive airways diseases and conditions to which the present invention is applicable include acute lung injury (ALI), adult respiratory distress syndrome (ARDS), chronic obstructive pulmonary, airways or lung disease (COPD, COAD or COLD), including chronic bronchitis or dyspnea associated therewith, emphysema, as well as exacerbation of airways hyper-reactivity consequent to other drug therapy, in particular other inhaled drug therapy. The invention is also applicable to the treatment of bronchitis of whatever type or genesis including, e.g., acute, arachidic, catarrhal, croupus, chronic or phthinoid bronchitis. Further inflammatory or obstructive airways diseases to which the present invention is applicable include pneumoconiosis (an inflammatory, commonly occupational, disease of the lungs, frequently accompanied by airways obstruction, whether chronic or acute, and occasioned by repeated inhalation of dusts) of whatever type or genesis, including, for example, aluminosis, anthracosis, asbestosis, chalicosis, cystic fibrosis, ptilosis, siderosis, silicosis, tabacosis and byssinosis.

Having regard to their anti-inflammatory activity, in particular in relation to inhibition of eosinophil activation, agents of the invention are also useful in the treatment of eosinophil related disorders, e.g. eosinophilia, in particular eosinophil related disorders of the airways (e.g. involving morbid eosinophilic infiltration of pulmonary tissues) including hyper-eosinophilia as it effects the airways and/or lungs as well as, for example, eosinophil-related disorders of the airways consequential or concomitant to Löffler's syndrome, eosinophilic pneumonia, parasitic (in particular metazoan) infestation (including tropical. eosinophilia), bronchopulmonary aspergillosis, polyarteritis nodosa (including Churg-Strauss syndrome), eosinophilic granuloma and eosinophil-related disorders affecting the airways occasioned by drug-reaction.

Agents of the invention are also useful in the treatment of inflammatory or allergic conditions of the skin, for example psoriasis, contact dermatitis, atopic dermatitis, alopecia areata, erythema multiforma, dermatitis herpetiformis, scleroderma, vitiligo, hypersensitivity angiitis, urticaria, bullous pemphigoid, lupus erythematosus, pemphisus, epidermolysis bullosa acquisita, and other inflammatory or allergic conditions of the skin.

Agents of the invention may also be used for the treatment of other diseases or conditions, in particular diseases or conditions having an inflammatory component, for example, treatment of diseases and conditions of the eye such as conjunctivitis, keratoconjunctivitis sicca, and vernal conjunctivitis, diseases affecting the nose including allergic rhinitis, and inflammatory disease in which autoimmune reactions are implicated or having an autoimmune component or aetiology, including autoimmune haematological disorders (e.g. haemolytic anaemia, aplastic anaemia, pure red cell anaemia and idiopathic thrombocytopenia), systemic lupus erythematosus, polychondritis, sclerodoma, Wegener granulamatosis, dermatomyositis, chronic active hepatitis, myasthenia gravis, Steven-Johnson syndrome, idiopathic sprue, autoimmune inflammatory bowel disease (e.g. ulcerative colitis and Crohn's disease), endocrine opthalmopathy, Grave's disease, sarcoidosis, alveolitis, chronic hypersensitivity pneumonitis, multiple sclerosis, primary billiary cirrhosis, uveitis (anterior and posterior), keratoconjunctivitis sicca and vernal keratoconjunctivitis, interstitial lung fibrosis, psoriatic arthritis and glomerulonephritis (with and without nephrotic syndrome, e.g. including idiopathic nephrotic syndrome or minal change nephropathy).

Other diseases or conditions which may be treated with agents of the invention include septic shock, rheumatoid arthritis, osteoarthritis, proliferative diseases such as cancer, atherosclerosis, allograft rejection following transplantation, stroke, obesity, restenosis, diabetes, e.g. diabetes mellitus type I (uvenile diabetes) and diabetes mellitus type II, diarrhoeal diseases, ischemia/reperfusion injuries, retinopathy, such as diabetic retinopathy or hyperbaric oxygen-induced retinopathy, and conditions characterised by elevated intraocular pressure or secretion of ocular aqueous humor, such as glaucoma.

The effectiveness of an agent of the invention in inhibiting inflammatory conditions, for example in inflammatory airways diseases, may be demonstrated in an animal model, e.g. a mouse or rat model, of airways inflammation or other inflammatory conditions, for example as described by Szarka et al, *J. Immunol. Methods* (1997) 202:49-57; Renzi et al, *Am. Rev. Respir. Dis.* (1993) 148:932-939; Tsuyuki et al., *J. Clin. Invest.* (1995) 96:2924-2931; and Cernadas et al (1999) *Am. J. Respir. Cell Mol. Biol.* 20:1-8.

The agents of the invention are also useful as co-therapeutic agents for use in combination with other drug substances such as anti-inflammatory, bronchodilatory or antihistamiine drug substances, particularly in the treatment of obstructive or inflammatory airways diseases such as those mentioned hereinbefore, for example as potentiators of therapeutic activity of such drugs or as a means of reducing required dosaging or potential side effects of such drugs. An agent of the invention may be mixed with the other drug substance in a fixed pharmaceutical composition or it may be administered separately, before, simultaneously with or after the other drug substance. Accordingly the invention includes a combination of an agent of the invention as hereinbefore described with an anti-inflammatory, bronchodilatory, antihistamine or antitussive drug substance, said agent of the invention and said drug substance being in the same or different pharmaceutical composition.

Suitable anti-inflammatory drugs include steroids, in particular glucocorticosteroids such as budesonide, beclamethasone dipropionate, fluticasone propionate, ciclesonide or mometasone furoate, or steroids described in WO 02/88167, WO 02/12266, WO 02/100879, WO 02/00679 (especially those of Examples 3, 11, 14, 17, 19, 26, 34, 37, 39, 51, 60, 67, 72, 73, 90, 99 and 101), WO 03/035668, WO 03/048181, WO 03/062259, WO 03/064445, WO 03/072592, non-steroidal glucocorticoid receptor agonists such as those described in WO 00/00531, WO 02/10143, WO 03/082280, WO 03/082787, WO 03/104195, WO 04/005229; LTB4 antagonists such LY293111, CGS025019C, CP-195543, SC-53228, BIIL 284, ONO 4057, SB 209247 and those described in U.S. Pat. No. 5451700; LTD4 antagonists such as montelukast and zafirlukast; PDE4 inhibitors such cilomilast (Ariflo® GlaxoSmithKline), Roflumilast (Byk Gulden),V-11294A (Napp), BAY19-8004 (Bayer), SCH-351591 (Schering-Plough), Arofylline (Almirall Prodesfarma), PD189659/PD168787 (Parke-Davis), AWD-12-281 (Asta Medica), CDC-801 (Celgene), SelCID(TM) CC-10004 (Celgene), VM554/UM565 (Vernalis), T-440 (Tanabe), KW-4490 (Kyowa Hakko Kogyo), and those disclosed in WO 92/19594, WO 93/19749, WO 93/19750, WO 93/19751, WO 98/18796, WO 99/16766, WO 01/13953, WO 03/104204, WO 03/104205, WO 03/39544, WO 04/000814, WO 04/000839, WO 04/005258, WO 04/018450, WO 04/018451, WO 04/018457, WO 04/018465, WO 04/018431, WO 04/018449, WO 04/018450, WO 04/018451, WO 04/018457, WO 04/018465, WO 04/019944, WO 04/019945, WO 04/045607 and WO 04/037805; A2a agonists such as those disclosed in EP 409595A2, EP 1052264, EP 1241176, WO 94/17090, WO 96/02543, WO 96/02553, WO 98/28319, WO 99/24449, WO 99/24450, WO 99/24451, WO 99/38877, WO 99/41267, WO 99/67263, WO 99/67264, WO 99167265, WO 99/67266, WO 00/23457, WO 00/77018, WO 00/78774, WO 01/23399, WO 01/27130, WO 01/27131, WO 01/60835, WO 01/94368, WO 02/00676, WO 02/22630, WO 02/96462, WO 03/086408, WO 04/039762, WO 04/039766, WO 04/045618 and WO 04/046083; A2b antagonists such as those described in WO 02/42298; and beta-2 adrenoceptor agonists such as albuterol (salbutamol), metaproterenol, terbutaline, salmeterol fenoterol, procaterol, and especially, formoterol and pharmaceutically acceptable salts thereof, and compounds (in free or salt or solvate form) of formula I of WO 0075114, which document is incorporated herein by reference, preferably compounds of the Examples thereof, especially a compound of formula

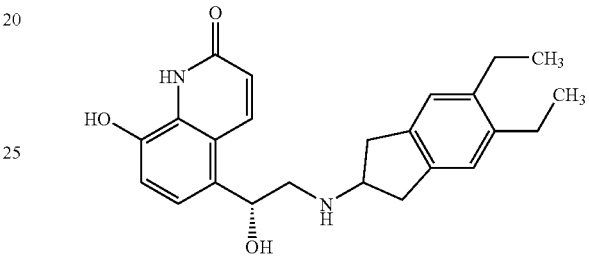

and pharmaceutically acceptable salts thereof, as well as compounds (in free or salt or solvate form) of formula I of WO 04/16601, and also compounds of WO 04/033412.

Suitable bronchodilatory drugs include anticholinergic or antimuscarinic agents, in particular ipratropium bromide, oxitropium bromide, tiotropium salts and CHF 4226 (Chiesi), and glycopyrrolate, but also those described in WO 01/04118, WO 02/51841, WO 02/53564, WO 03/00840, WO 03/87094, WO 04/05285, WO 02/00652, WO 03/53966, EP 424021, U.S. Pat. No. 5,171,744, U.S. Pat. No. 3,714,357, WO 03/33495 and WO 04/018422.

Suitable antihistamine drug substances include cetirizine hydrochloride, acetaminophen, clemastine fumarate, promethazine, loratidine, desloratidine, diphenhydramine and fexofenadine hydrochloride, activastine, astemizole, azelastine, ebastine, epinastine, mizolastine and tefenadine as well as those disclosed in WO 03/099807, WO 04/026841 and JP 2004107299.

Other useful combinations of agents of the invention with anti-inflammatory drugs are those with antagonists of chemokine receptors, e.g. CCR-1, CCR-2, CCR-3, CCR-4, CCR-5, CCR-6, CCR-7, CCR-8, CCR-9 and CCR10, CXCR1, CXCR2, CXCR3, CXCR4, CXCR5, particularly CCR-5 antagonists such as Schering-Plough antagonists SC-351125, SCH-55700 and SCH-D, Takeda antagonists such as N-[[4-[[[6,7-dihydro-2-(4-methylphenyl)-5H-benzocyclohepten-8-yl]carbonyl]amino]phenyl]-methyl]tetrahydro-N,N-dimethyl-2H-pyran-4-aminium chloride (TAK-770), and CCR-5 antagonists described in U.S. Pat. No. 6,166,037 (particularly claims 18 and 19), WO 00/66558 (particularly claim 8), WO 00/66559 (particularly claim 9), WO 04/018425 and WO 04/026873.

The agents of the invention may be administered by any appropriate route, e.g. orally, for example in the form of a tablet or capsule; parenterally, for example intravenously; by inhalation, for example in the treatment of inflammatory or obstructive airways disease; intranasally, for example in the treatment of allergic rhinitis; topically to the skin, for example in the treatment of atopic dermatitis; or rectally, for example in the treatment of inflammatory bowel disease.

The present invention also provides a pharmaceutical composition comprising a compound of formula I in free form or in the form of a pharmaceutically acceptable salt, optionally together with a pharmaceutically acceptable diluent or carrier therefor. The composition may contain a co-therapeutic agent such as an anti-inflammatory, bronchodilatory or antihistamine drug as hereinbefore described. Such compositions may be prepared using conventional diluents or excipients and techniques known in the galenic art. Thus oral dosage forms may include tablets and capsules. Formulations for topical administration may take the form of creams, ointments, gels or transdermal delivery systems, e.g. patches. Compositions for inhalation may comprise aerosol or other atomizable formulations or dry powder formulations.

When the composition comprises an aerosol formulation, it preferably contains, for example, a hydro-fluoro-alkane (HFA) propellant such as HFA134a or HFA227 or a mixture of these, and may contain one or more co-solvents known in the art such as ethanol (up to 20% by weight), and/or one or more surfactants such as oleic acid or sorbitan trioleate, and/or one or more bulking agents such as lactose. When the composition comprises a dry powder formulation, it preferably contains, for example, the compound of formula I having a particle diameter up to 10 microns, optionally together with a diluent or carrier, such as lactose, of the desired particle size distribution and a compound that helps to protect against product performance deterioration due to moisture e.g. magnesium stearate. When the composition comprises a nebulised formulation, it preferably contains, for example, the compound of formula I either dissolved, or suspended, in a vehicle containing water, a co-solvent such as ethanol or propylene glycol and a stabiliser, which may be a surfactant.

The invention includes (A) an agent of the invention in inhalable form, e.g. in an aerosol or other atomisable composition or in inhalable particulate, e.g. micronised form, (B) an inhalable medicament comprising an agent of the invention in inhalable form; (C) a pharmaceutical product comprising such an agent of the invention in inhalable form in association with an inhalation device; and (D) an inhalation device containing an agent of the invention in inhalable form.

Dosages of agents of the invention employed in practising the present invention will of course vary depending, for example, on the particular condition to be treated, the effect desired and the mode of administration. In general, suitable daily dosages for oral administration are of the order of 0.1 to 10 mg/kg.

EXAMPLES

Abbreviations used are as follows: CDI is 1,1'-carbonyldiimidazole, DCM is dichloromethane, DIPEA is diisopropylethylamine, DMF is Dimethylformamide, THF is tetrahydrofuran, HPLC is High Performance Liquid Chromatography, DMF-DMA is N,N-Dimethylformamide dimethylacetal, DMSO is dimethyl sulfoxide, HCl is Hydrochloric acid, TFA is Trifluoroacetic acid. HOBT is Hydroxy benzotriazole, and HOAt is Hydroxy azabenzotriazole.

Preparation of Intermediates

The following aminothiazole intermediates of formula (A)

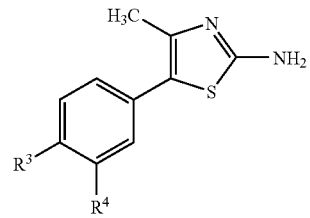

A are shown in Table 1 below, their method of preparation being described hereinafter.

TABLE 1

| Intermediate | $R^3$ | $R^4$ | M/s MH+ |
|---|---|---|---|
| AA | —SO$_2$CH$_3$ | F | 287.11 |
| AB | —SO$_2$CH$_3$ | CF$_3$ | 337.00 |
| AC | —SO$_2$CH$_3$ | Cl | 302.99 |
| AD | —SO$_2$CH$_3$ | CN | 294.02 |
| AE | —SO$_2$CH$_3$ | H | 268.90 |
| AF | —SO$_2$CH$_3$ | imidazol-1-yl | 335.07 |
| AG | F | —SO$_2$CH$_3$ | 286.99 |

The amines that are used to prepare the final compounds of Examples in Tables 4 & 5 are commercially available or are prepared by standard methods. The amines exemplified in Table 3 and used to prepare the final compounds of the Examples in Table 6 are not readily commercially available, the methods of preparation being described below.

Intermediate AA 5-(3-Fluoro-4-methanesulfonyl-phenyl)-4-methyl-thiazol-2-ylamine AA1) 3-Fluoro4-methanesulfonyl-benzaldehyde Methane sulfinic acid sodium salt (20.1 g, 200 mmol) is added to a stirred solution of 3,4-difluorobenzaldehyde (22.5 g, 158 miol) in dry DMSO (200 ml) at 75° C. After 2 hours the reaction is poured onto ice-water (200 ml). The precipitate is filtered, washed with water and dissolved in chloroform (400 ml). The organic extract is washed with water (2×200 ml), dried over MgSO$_4$, filtered, and the solvent is removed to give the title compound as a white solid.

AA2) 2-Fluoro-1-methanesulfonyl-4-(2-nitro-propenyl)-benzene

A stirred mixture of 3-fluoro-4-methanesulfonyl-benzaldehyde (Example AA1) (24 g, 0.119 mol), nitroethane (70 ml, 0.97 mol) and ammonium acetate (2.75 g, 35 mmol) is heated at reflux under argon for 24 hours. The mixture is concentrated to give an oil which is dissolved in chloroform (200 ml) and washed with water (2×200 ml), followed by brine (100 ml). The organic extract is dried (MgSO$_4$), filtered and the solvent removed to give the product as an orange oil. This was used immediately in the next step.

AA3) 1-(3-Fluoro-4-methanesulfonyl-phenyl)-propan-2-one

Iron powder (25 g, 0.45 mol) is added to a stirred mixture of freshly prepared 2-fluoro-1-methanesulfonyl4-(2-nitropropenyl)-benzene (Example AA2) (29 g, 0.112 mol) in THF (50 ml). Water (110 ml) is added and the mixture is heated to 60° C. Concentrated hydrochloric acid (50 ml) is added slowly over 1 h at 60-90° C. The reaction is then stirred at 100° C. for 20 hours then diluted with cold water (500 ml) and filtered through Celite™ filter material washing with chloroform (500 ml). he organic extract is washed with water (200 ml) followed by brine (200 ml). After drying (MgSO$_4$) the mixture is absorbed on silica and purified by chromatography, eluting with hexane-ethyl acetate (1:1) to give the titled compound.

AA4) 5-(3-Fluoro-4-methanesulfonyl-phenyl)4methyl-thiazol-2-ylamine 1-(3-Fluoro-4-methanesulfonyl-phenyl)-propan-2-one (AA3) (1.0 g, 4.34 mmol) is dissolved in dioxane (35 ml) and the solution is cooled to 10° C. at which point the mixture is semi frozen. Bromine (0.201 ml, 3.6 mmol, 0.8 eq.) is added slowly and the mixture is stirred for an additional 15 min in a semi frozen state. The mixture is then allowed to warm to room temperature and the solvent is removed to give a brown oil containing starting material and 1-bromo-1-(3-fluoro-4-methanesulfonyl-phenyl)-propan-2-one. This material is dissolved in ethanol (30 ml) and thiourea (0.236 g, 3.1 mmol) is added in one portion. The mixture is stirred at 60° C. for 30 minutes then allowed to cool whereupon the product crystallised. Filtration affords the hydrobromide salt of the product as a white solid. The free base is prepared by dissolving the hydrobromide salt in dilute aqueous hydrochloric acid and adding sodium hydroxide solution until alkaline. The title compound precipitates as the free base.

Intermediate AB

5-(4-Methanesulfonyl-3-trifluoromethyl-phenyl)-4-methyl-thiazol-2-ylamine

AB1) N-[5-(4-Methanesulfonyl-3-trifluoromethyl-phenyl)-4-methyl-thiazol-2-yl]-acetamide The titled compound is made via an analogous method to 5-(3-Fluoro-4-methanesulfonyl-phenyl)-4-methyl-thiazol-2-ylamine (Example AA) by replacing 3,4-difluorobenzaldehyde (step AA1) with 4-chloro-3-trifluoromethyl-benzaldehyde, and thiourea (step AA4) with N-acetylthiourea.

AB2) 5-(4-Methanesulfonyl-3-trifluoromethyl-phenyl)4-methyl-thiazol-2-ylamine N-[5-(4-Methanesulfonyl-3-trifluorome)yl-phenyl)4-methyl-thiazol-2-yl]-acetamide (AB1) (0.115 g, 0.3 mmol) is suspended in ethanol (5 ml). Hydrochloric acid (1.58 ml, 6N HCl) is added and the reaction mixture is heated at reflux for two hours. The solvent is removed in vacuo and the crude residue is suspended in water and sodium hydroxide solution is added until the pH is adjusted to pH 13-14. The yellow precipitate is stirred at room temperature for 45 minutes and then filtered, washed with water and dried in vacuo to yield the titled compound.

Intermediate AC

5-(3-Chloro-4-methanesulfonyl-phenyl)-4methyl-thiazol-2-ylamine

This material is prepared by the procedure outlined in Experiment AA, replacing 3,4-difluorobenzaldehyde in the first step (AA1) with 3,4-dichloro-benzaldehyde.

Intermediate AD

5-(2-Amino-4-methyl-thiazol-5-yl)-2-methanesulfonyl-benzonitrile

This material is prepared by the procedure outlined in Experiment AA, replacing 3,4-difluorobenzaldehyde in the first step (AA1) with 2-fluoro-5-formyl-benzonitrile.

Intermediate AE

5-(4-Methanesulfonyl-phenyl)-4-methyl-thiazol-2-ylamine

AE1) N[5-(4-Amino-phenyl)-4-methyl-thiazol-2-yl]-acetamide

N-[4-Methyl-5-(4nitro-phenyl)-thiazol-2-yl]-acetamide (J. Liebscher, E. Mitzner, *Synthesis*, 1985, (4), p 414) (10.0 g, 3.6 mmol) is dissolved in ethyl acetate/THF (5/1, 600 ml) and stirred at room temperature under an atmosphere of argon. The solution is then treated with 10% palladium on carbon (10 g). The reaction mixture is purged three times with nitrogen and placed under an atmosphere of hydrogen overnight. The mixture is then filtered through Celite™ filter material and the catalyst is washed with tetrahydrofuran (600 ml). The solvent is removed in vacuo to leave N-[5-(4-amino-phenyl) 4-methyl-thiazol-2-yl]-acetamide as an off-white solid.

AE2) 4-(2-Acetylamino-4-methyl-thiazol-5-yl)-benzenesulfonyl chloride

N-[5-(4-Amino-phenyl)-4-methyl-thiazol-2-yl]-acetamide (AE1) (7.9 g, 31.9 mmol) in suspension in glacial acetic acid (250 ml) is treated with a 32% aqueous HCl solution (40 ml). The resulting solution is then cooled approximately to 10° C. and treated dropwise with a solution of sodium nitrite (2.2 g, 31.9 mmol) in water (2 ml). After 10 minutes the reaction mixture is added to a stirred solution of SO$_2$/AcOH/CuCl$_2$/H$_2$O (200 ml) (the preparation of the reagent is described below). The reaction mixture is allowed to warm to room temperature. After stirring overnight the reaction mixture is poured into water (1000 ml) and extracted with ethyl acetate (3×300 ml). The combined organic layers are washed with water (2×250 ml) followed by brine (200 ml) and dried over MgSO$_4$. After filtration the solvent is removed in vacuo to give the titled compound.

Preparation of the reagent SO$_2$/AcOH/CuCl$_2$/H$_2$O

According to the reported procedure (E. E. Gilbert, Synthesis 1969, 1-10, p 6), glacial acetic acid (100 ml) vigorously stirred at room temperature is treated by bubbling SO$_2$ gas. Once a saturated solution is achieved (approximately 10 g per 100 ml), the solution is treated with copper (II) chloride (4 g) in water (5 ml). The resulting miuure is allowed to settle to give a green solution.

AE3) 5-(4-Methanesulfonyl-phenyl)-4-methyl-thiazol-2-ylamine 4-(2-Acetylamino-methyl-thiazol-5-yl)-benzenesulfonyl chloride (AE2) (0.5 g, 1.5 mmol) in dioxane (2 ml) is added dropwise to a stirred solution of sodium sulfite (0.378 g, 3.0 mmol) and sodium hydrogen carbonate (0.252 g, 3.0 mmol) in water at 75° C. After 1 hour at 75° C., bromoacetic acid (0.417 g, 3.0 mmol) is added and heating continued for 1 hour at 100° C. Sodium hydroxide (0.24 g, 6.0 mmol) in water (0.25 ml) is then added and the mixture is heated with stirring at 90° C. for 16 hours. The reaction mixture is allowed to cool, diluted with water (100 ml) and extracted with dichloromethane (3×75 ml). The combined organic extracts are washed with brine (75 ml), dried (MgSO$_4$), filtered, and the solvent removed to give the title compound.

Intermediate AF

5-(3-Imidazol-1-yl-4-methanesulfonyl-phenyl)4-methyl-thiazol-2-ylamine

AF1) N-[5-(3-fluoro-4-methanesulfonyl-phenyl)-4-methyl-thiazol-2-yl]-acetamide This material is prepared from 1-(3-fluoro-4-methanesulfonyl-phenyl)-propan-2-one (AA3) following the procedure outlined in step (AA4), replacing thiourea with N-acetylthiourea. The titled compound crystallises from the reaction mixture.

AF2) N-[5-(3-Imidazol-1-yl-4-methanesulfonyl-phenyl)-4-methyl-thiazol-2-yl]-acetamide A stirred mixture of N-[5-(3-fluoro-4-methanesulfonyl-phenyl)-4-methyl-thiazol-2-yl]-acetamide (AF1) (5.0 g, 15 mmol), imidazole (2.07 g, 30 mmol) and caesium carbonate (9.93 g, 30 mmol) in dry NMP (30 ml) is heated under argon at 135° C. for 18 hours. The reaction mixture is then poured onto water (50 ml) whereupon the titled product precipitates and is recrystalfised from ethanol-water.

AF3) 5-(3-Imidazol-1-yl-4-methanesulfonyl-phenyl)-4-methyl-thiazol-2-ylamine N-[5-(3-Imidazol-1-yl-4-methanesulfonyl-phenyl)-4-methyl-thiazol-2-yl]-acetamide (AF2) (5.0 g, 13 mmol) is dissolved in 7M HCl (50 ml) and the solution is heated at 100° C. for 3 h. When cool the solution is brought to pH 8 by addition of aqueous NaOH whereupon the titled product precipitates. This is washed with ethanol followed by EtOAc, Et$_2$O and dried.

Intermediate AG

5-(4-Fluoro-3-methanesulfonyl-phenyl)-4-methyl-thiazol-2-ylamine

AG1) 2-Fluoro-5-(2-oxo-propyl)-benzenesulfonyl chloride

To a stirred flask of chlorosulphonic acid (344 g, 2.96 mol) cooled to −10° C. is added dropwise 1-(4-fluoro-phenyl)-propan-2-one (10 g, 65 mmol). The reaction mixture is left stirring at room temperature overnight and then poured carefully onto ice. The resultant solution is extracted with ethyl acetate and the organic extracts combined, dried (MgSO$_4$) and concentrated in vacuo to yield the titled compound.

AG2) 2-Fluoro-5-(2-oxo-propyl)-benzenesulfinic acid sodium salt

To a stirred solution of 2-fluoro-5-(2-oxo-propyl)-benzenesulfonyl chloride (AG1) (16.25 g, 86.36 mmol) in dioxane (200 ml) is added dropwise a solution of sodium sulfite (16.38 g, 130 mmol) and sodium hydrogen carbonate (10.92 g, 130 mmol) in water (200 ml). The reaction mixture is heated to 70° C. for 20 minutes and then allowed to cool to room temperature. The solvent is removed in vacuo and the resultant residue is used crude in the next step.

AG3) 1-(4-Fluoro-3-methanesulfonyl-phenyl)-propan-2-one

A solution comprising 2-fluoro-5-(2-oxo-propyl)-benzenesulfinic acid sodium salt (AG2) (15.43 g, 64.83 mmol) in DMF (300 ml) is treated with methyl iodide (18.45 g, 130 mmol). The reaction mixture is stirred at room temperature for 30 minutes. Purification is carried out by chromatography on silica (eluting with 4:1 hexane-ethyl acetate) to afford the titled compound.

AG4) 5-(4-Fluoro-3-methanesulfonyl-phenyl)-4-methyl-thiazol-2-ylamine

The titled compound is prepared via an analogous method to 5-(3-fluoro-4-methanesulfonyl-phenyl)-4-methyl-thiazol-2-ylamine (Intermediate AA) by replacing 1-(3-fluoro-4-methanesulfonyl-phenyl)-propan-2-one (AA3) in step AA4 with 1-(4-fluoro-3-methanesulfonyl-phenyl)-propan-2-one (AG3).

The following imidazole-urea intermediates of formula (B)

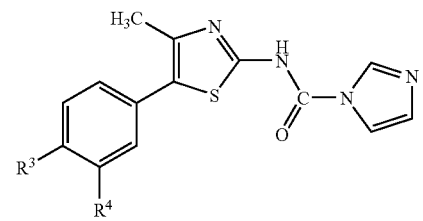

are shown in the Table 2 below, the method of preparation being described hereinafter.

TABLE 2

| Intermediate | R$^3$ | R$^4$ | Starting material | Method |
|---|---|---|---|---|
| BA | —SO$_2$CH$_3$ | F | AA | Ba |
| BB | —SO$_2$CH$_3$ | CF$_3$ | AB | Ba |
| BC | —SO$_2$CH$_3$ | Cl | AC | Ba |
| BD | —SO$_2$CH$_3$ | CN | AD | Bb |
| BE | —SO$_2$CH$_3$ | H | AE | Ba |
| BF | —SO$_2$CH$_3$ | imidazol-1-yl | AF | Bb |
| BG | F | —SO$_2$CH$_3$ | AG | Ba |

Method (Ba)

A suspension of the aminothiazole (17.5 mmol) and 1,1'-carbonyldiimidazole (4.26 g, 26.3 mmol, 1.5 equivalents) in CH$_2$Cl$_2$ (100 ml) is heated at 40° C.—reflux under argon until no starting material remains (30 min-5 hours) as determined by HPLC and NMR. When cool the solid precipitate is removed by filtration. This solid consists of the imidazole-urea intermediate (B) together with variable amounts of the corresponding isocyanate and imidazole which result from reversible thermal elimination of imidazole under the reaction conditions. This solid is used in the subsequent steps since the imidazole-urea intermediate and isocyanate intermediate are equally suitable as precursors to ureas.

The following intermediates are prepared by this method, namely: Imidazole-1-carboxylic acid [5-(3-fluoro-4-methanesulfonyl-phenyl)-4-methyl-thiazol-2-yl]-amide (BA), Imidazole-1-carboxylic acid [5-(4-methanesulfonyl-3-trifluoromethyl-phenyl)-4-methyl-thiazol-2-yl]-amide (BB), Imidazole-1-carboxylic acid [5-(3-chloro-4-methanesulfonyl-phenyl)-4-methyl-thiazol-2-yl]-amide (BC), Imidazole-1-carboxylic acid [5-(4-methanesulfonyl-phenyl)-4-methyl-thiazol-2-yl]-amide (BE) and Imidazole-1-carboxylic acid [5-(4-fluoro-3-methanesulfonyl-phenyl)-4-methyl-thiazol-2-yl]-amide (BG).

Method (Bb)

Triethylamine or sodium hydride (1.25 equivalents) is added to a stirred suspension of the aminothiazole (7.5 mmol) and carbonyldiimidazole (1.3 g, 8.2 mmol, 1.1 equivalents) in dry CH$_2$Cl$_2$ (40 ml) containing a few drops of DMF to aid solubility. The reaction is heated at reflux under argon until no starting material remains (18 h) as determined by HPLC and NMR. When cool the solid precipitate is removed by filtration and washed with diethyl ether. This solid consists of the carbonyl diimidazole intermediate (B) together with variable amounts of the corresponding isocyanate and imidazole which result from thermal elimination of imidazole under the reaction conditions. This solid is used in the subsequent steps since the CDI intermediate (B) and isocyanate intermediate are equally suitable as precursors to ureas.

The following intermediates were prepared by this method: Imidazole-1-carboxylic acid [5-(3-cyano-4-methanesulfonyl-phenyl)-4-methyl-thiazol-2-yl]-amide (BD) and Imidazole-1-carboxylic acid [5-(3-imidazol-1-yl-4-methanesulfonyl-phenyl)-4-methyl-thiazol-2-yl]-amide (BF).

The following amine intermediates of formula (C)

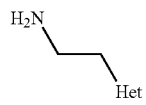

C

Where Het. =

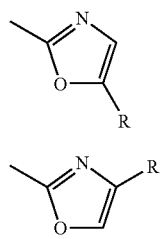 CA

CB

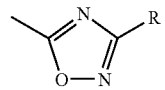 CC

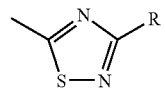 CD

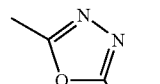 CE

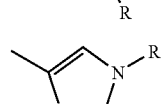 CF

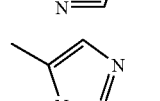 CG

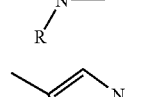 CH

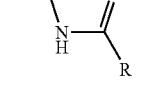 CI

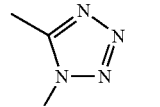 CJ are shown in the Table 3 below, the method of preparation being described hereinafter.

TABLE 3

| Intermediate | Het | R |
|---|---|---|
| CA1 | CA | —CH$_2$CH$_3$ |
| CA2 | CA | —CH$_3$ |
| CA3 | CA | —C(CH$_3$)$_3$ |
| CB1 | CB | —CH$_3$ |
| CB2 | CB | —CH$_2$CH$_3$ |
| CC1 | CC | —CH$_3$ |
| CC2 | CC | —CH$_2$CH$_3$ |
| CC3 | CC | —CH$_2$CH$_2$CH$_3$ |
| CC4 | CC | —CH(CH$_3$)$_2$ |
| CC5 | CC | -Cyclopropyl |
| CC6 | CC | —C(CH$_3$)$_3$ |
| CC7 | CC | —CH$_2$N(CH$_3$)$_2$ |
| CD1 | CD | —CH$_3$ |
| CE1 | CE | —CH$_3$ |
| CE2 | CE | —CH$_2$CH$_3$ |
| CE3 | CE | —CH$_2$CH$_2$CH$_3$ |
| CE4 | CE | —CH(CH$_3$)$_2$ |
| CE5 | CE | -Cyclopropyl |
| CE6 | CE | -Cyclobutyl |
| CE7 | CE | —C(CH$_3$)$_3$ |
| CF1 | CF | —CH$_2$CH$_3$ |
| CG1 | CG | —CH$_2$CH$_3$ |
| CH1 | CH | —C(CH$_3$)$_3$ |
| CH2 | CH | —CH(CH$_3$)$_2$ |
| CI1 | CI | —H |

TABLE 3-continued

| Intermediate | Het | R |
|---|---|---|
| CI2 | CI | —CH$_2$CH$_3$ |
| CJ1 | CJ | —CH$_2$CH$_3$ |

Intermediate CA1

2-(5-Ethyl-oxazol-2-yl)-ethylamine

Step 1: [2-(2-Hydroxy-butylcarbamoyl)-ethyl]-carbamic acid benzyl ester

A mixture comprising Z-Beta-Ala-OH (9.0 g, 40.3 mmol), EDCI.HCl (10.0 g, 52.4 mmol), hyrdoxybenzotriazole (5.45 g, 40.3 mmol), triethylamine (7.3 ml, 52.4 mnmol) in DCM (150 ml) is stirred at 0° C. for 30 minutes. 1-Amino-2-butanol (4.2 ml, 44.3 mmol) is added in one portion and stirring is continued for 1 hour. The reaction mixture is diluted with water (150 ml) and extracted with dichloromethane (2×150 ml). The organic layers are combined, dried over MgSO$_4$, filtered and concentrated in vacuo to yield a crude white solid. The product is purified by chromatography on silica eluting with ethanol-ethyl acetate (1:10) to give the titled compound.

Step 2: [2-(2-Oxo-butylcarbamoyl)-ethyl]-carbamic acid benzyl ester

To a stirred solution of oxalyl chloride (2 M in DCM) (13.35 ml, 26.5 mmol) in dry DCM at −78° C. is added dropwise DMSO (2.5 ml, 35.4 mmol). After stirring for 15 minutes, the reaction mixture is treated with a solution of [2-(2-hydroxy-butylcarbamoyl)-ethyl]-carbamic acid benzyl ester (step 1) (6.5 g, 22.1 mol) in dry DCM (40 ml). Triethylamine (13 ml) is added after 1 hour and after stirring at −78° C. for 90 minutes, the reaction mixture is allowed to warm to room temperature. The reaction is diluted with DCM (100 ml) and washed with HCl (1M, 200 ml), saturated sodium bicarbonate solution (200 ml), water (200 ml) and brine (200 ml). The organic portion is dried over MgSO$_4$, filtered and concentrated in vacuo to yield the titled compound as a white solid.

Step 3: [2-(5-Ethyl-oxazol-2-yl)-ethyl]-carbamic acid benzyl ester

To a stirred suspension of polymer supported triphenylphosphene (19.6 g, 58.9 mmol) in DCM (250 ml) is added iodine (14.95 g, 58.9 mmol). After stirring at room temperature for 10 minutes, the mixture is treated with triethylamine (16.4 ml, 117.5 mmol) followed by a solution of [2-(2-oxo-butylcarbamoyl)-ethyl]-carbamic acid benzyl ester (step 2) (6.88 g, 23.5 mmol) in DCM (50 ml). The reaction mixture is stirred overnight and then filtered through Celite™ filter material, washed through with DCM (500 ml) and the solvent removed in vacuo to yield the titled compound as a brown solid.

Step 4: 2-(5-Ethyl-oxazol-2-yl)-ethylamine

Ammnonium formate (0.316 g, 5 mmol) is added to a solution of [2-(5-ethyl-oxazol-2-yl)-ethyl]-carbamic acid benzyl ester (step 3) (1.66 mmol) in methanol (15 ml) and 10% Pd on carbon (125 mg) is added under an inert atmosphere. The mixture is stirred at ambient temperature for 2 hours. The catalyst is removed by filtration and the filtrate is evaporated. The residue is diluted with dichloromethane, filtered to remove undissolved solid and the solvent is removed. The residue is dissolved in DCM and treated with 1M aqueous sodium hydroxide solution (5 ml). The organic extract is separated, dried (MgSO$_4$), filtered and the solvent is removed. Crystallisation from ethyl acetate/dichloromethane affords the titled compound.

Intermediate CA2

2-(5-Methyl-oxazol-2-yl)-ethylamine

This compound was made by an analogous procedure to 2-(5-ethyl-oxazol-2-yl)-ethylamine (CA1) by replacing 1-amino-2-butanol (CA1, step 1) with 1-amino-propan-2-ol.

Intermediate CA3

2-(5-tert-Butyl-oxazol-2-yl)-ethylamine

Step 1: 1-Azido-3,3-dimethyl-butan-2-ol

Sodium azide (10 g, 154 mmol) and ammonium chloride (3.7 g, 070 mmol) are added to a solution of 3,3-dimethyl-1,2-epoxybutane (4.26 ml, 35 mmol) in methanol:water (8:1, 315 ml), and the mixture is heated at reflux for 7 hours. The reaction is poured into ice/water (400 ml) and extracted with dichloromethane (3×200 ml). The combined organics are dried (MgSO$_4$), filtered and evaporated to yield a clear oil (4.7 g, 94%).

Step 2: 1-Amino-3,3-dimethyl-butan-2-ol

1-Azido-3,3-diinethyl-butan-2-ol (4.7 g, 33 mmol) in ethanol (200 ml) is stirred under hydrogenated for 36 h in the presence of 10% palladium on carbon. The catalyst is removed by filtration and the filtrate is evaporated to give the titled compound as a colourless crystalline solid (2.7 g, 69%). The final compound (CA3) is then prepared by an analogous procedure to 2-(5-ethyl-oxazol-2-yl)-ethylamine (CA1) by replacing 1-amino-2-butanol (CA1, step 1) with 1-amino-3,3-dimethyl-butan-2-ol.

Intermediates CB1 & CB2

These compounds, namely 2-(4-methyl-oxazol-2-yl)-ethylamine (CB1) and 2-(4-ethyl-oxazol-2-yl)-ethylamine (CB2) are prepared by an identical procedure to 2-(5-Ethyl-oxazol-2-yl)-ethylarnine (CA1) by replacing 1-amino-2-butanol (CA1, step 1) in this procedure with 2-amino-1-butanol (for CB1) and 2-amino-1-propanol (for CB2) respectively.

Intermediates CC1-CC7

These compounds, namely, 2-(3-Methyl-[1,2,4]oxadiazol-5-yl)-ethylamine (CC1), 2-(3-Ethyl-[1,2,4]oxadiazol-5-yl)-ethylamine (CC2), 2-(3-Propyl-[1,2,4]oxadiazol-5-yl)-ethylamine (CC3), 2-(3-Isopropyl-[1,2,4]oxadiazol-5-yl)-ethylamine (CC4), 2-(3-Cyclopropyl-[1,2,4]oxadiazol-5-yl)-ethylamine (CC5), 2-(3-tert-Butyl-[1,2,4]oxadiazol-5-yl)-ethylamine (CC6) and 2-(3-Dimethylaminomethyl-[1,2,4]oxadiazol-5-yl)-ethylamine (CC7) are prepared by an identical procedure starting from the appropriate nitrile. This is exemplified by the preparation of intermediate CC3. Preparation of the nitrile used for intermediate CC7 is described in C. S. Hollander; R. A. Yoncoskie & P. L. deBenneville, *J. Org. Chem.*, (1958) 23, 112-215.

Intermediate CC3

2-(3-Propyl-[1,2,4]oxadiazol-5-yl)-ethylamine

Step 1: N-Hydroxy-butyramidine

Ethanol (80 ml) followed by hydroxylamine hydrochloride (4.0 g, 57 mmol) is added to a solution of $K_2CO_3$ (7.9 g, 57 mmol) in water (25 ml). Butyronitrile (5.0 ml, 57 mmol) is then added and the mixture is heated at reflux for 18 h. After cooling, the solvent is removed in vacuo and ethanol is added to dissolve the product. The solution is separated from any undissolved solid and the solvent is removed to leave the titled compound as a yellow oil.

Step 2: [2-(3-Propyl-[1,2,4]oxadiazol-5-yl)-ethyl]-carbamic acid tert-butyl ester N-Hydroxy-butyramidine (0.425 g, 4.16 mmol) in DMF (2 ml) is added to a stirred suspension of sodium hydride (0.183 g of a 60% dispersion in oil, 4.58 mmol) in the presence of molecular sieves (0.4 g). The reaction flask is then immersed in a pre-heated oil bath at 50° C. and stirring continued for 5 min. 3-tert-Butoxycarbonylamino-propionic acid ethyl ester (0.904 g, 4.16 mmol) in DMF (2 ml) is added over 5 min followed by more DMF (2 ml). After 3 h at 50° C. the mixture is cooled to 0° C. and water (3 ml) is added. The mixture is allowed to warm to room temperature then filtered through Celite™ filter material, washing with ethyl acetate, and the solvent is removed. Purification by chromatography, eluting with DCM:MeOH (95:5 increasing to 85:15) affords the titled compound.

Step 3: 2-(3-Propyl-[1,2,4]oxadiazol-5-yl)-ethylamine

TFA (6 ml) is added to a stirred solution of [2-(3-propyl-[1,2,4]oxadiazol-5-yl)-ethyl]-carbamic acid tert-butyl ester (0.67 g, 2.62 mmol) in DCM (10 ml). After 1 hor the solvents are removed to afford the titled compound.

Intermediate CD1

2-(3-Methyl-[1,2,4]thiadiazol-5-yl)-ethylamine

Step 1: [2-(1-Dimethylamino-ethylidenethiocarbamoyl)-ethyl]-carbamic acid tert-butyl ester Dimethylacetamide dimethylacetal (1.56 g, 11.7 mmol) is added to a stirred solution of (2-thiocarbamoyl-ethyl)-carbamic acid tert-butyl ester (1.0 g, 4.9 mmol) in DCM (50 ml). The reaction is stirred for 24 hours at room temperature followed by removal of the solvent. The residue is purified by chromatography on silica, eluting with ethyl acetate-diethyl ether (1:1) to give the titled compound as a yellow oil.

Step 2: 2-(3-Methyl-[1,2,4]thiadiazol-5-yl)-ethylamine

Hydroxylamine-O-sulfonic acid (0.68 g, 6.0 mmol) in methanol (5 ml) is added to a stirred solution of [2-(1-Dimethylamino-ethylidenethiocarbamoyl)-ethyl]-carbamic acid tert-butyl ester (1.43 g, 5.0 mmol) and pyridine (0.83 ml, 10 mmol) in ethanol (25 ml). After stirring the reaction for 18 hours at room temperature the solvent is removed in vacuo and the residue is partitioned between water and DCM. The organic extract is separated, dried ($MgSO_4$), and the solvent is removed to give a colourless oil which is dissolved in ethanol (20 ml). Aqueous HCl (2M, 10 ml) is added and the mixture is heated at reflux for 1 hour. After cooling to room temperature the solvent is removed. The product is dissolved in aqueous $NaHCO_3$ and the free base is extracted with ethyl acetate. The organic extract is dried ($MgSO_4$) and the solvent removed to give the titled compound.

Intermediate CE1

2-(5-Methyl-[1,3,4]oxadiazol-2-yl)-ethylamine

Step 1: [3-(N'-Acetyl-hydrazino)-3-oxo-propyl]-carbamic acid tert-butyl ester

EDCI.HCl (3.05 g, 15.95 mmol), HOBt (1.66 g, 12.27 mmol) and triethylamine (2.22 ml, 15.95 mmol) are added to a stirred solution of BOC-β-Ala-OH (2.32 g, 12.27 mmol) in DCM (60 ml). After stirring for 30 min at 0° C. acetic acid hydrazide (1.0 g, 13.5 mmol) is added in one portion. The reaction mixture is stirred at 0° C. for 1 hour. The reaction is diluted with water and extracted several times with DCM. The organic extract is dried ($MgSO_4$) and the solvent is removed to give an oil. Purification by chromatography on silica, eluting with EtOAc increasing to EtOAc:EtOH 10:1, affords the titled compound.

Step 2: [2-(5-Methyl-[1,3,4]oxadiazol-2-yl)-ethyl]-carbamic acid tert-butyl ester Iodine (0.261 g, 1.028 mmol) is added to a stirred solution of polymer supported triphenylphosphine (3 mmol/g, 0.34 g, 1.03 mmol) in DCM (10 ml). After stirring for 10 min at room temperature triethylamine (0.287 ml, 2.06 mmol) and [3-(N'-acetyl-hydrazino)-3-oxo-propyl]-carbamic acid tert-butyl ester (0.126 g, 0.514 mmol) are added. The reaction is stirred at room temperature for 18 h then filtered through a Celite™ filter material plug, washing with DCM. The solvent is removed and the residue is purified by chromatography on silica, eluting with EtOAc, to afford the titled compound.

Step 3: 2-(5-Methyl-[1,3,4]oxadiazol-2-yl)-ethylamine

TFA (1 ml) is added to a stirred solution of [2-(5-methyl-[1,3,4]oxadiazol-2-yl)-ethyl]-carbamic acid tert-butyl ester (0.077 g, 0.34 mmol) in DCM (5 ml). After 1 hour at room temperature the solvents are removed. The residue is dissolved in DCM and washed with 4M aqueous NaOH solution. The organic extract is separated, dried ($MgSO_4$) and the solvent removed to give the titled compound.

Intermediates CE2-CE7

These compounds, namely 2-(5-Ethyl-[1,3,4]oxadiazol-2-yl)-ethylamine (CE2), 2-(5-Propyl-[1,3,4]oxadiazol-2-yl)-ethylamine (CE3),2-(5-Isopropyl-[1,3,4]oxadiazol-2-yl)-ethylamine (CE4),2-(5-Cyclopropyl-[1,3,4]oxadiazol-2-yl)-ethylamine (CE5), 2-(5-Cyclobutyl-[1,3,4]-oxadiazol-2-yl)-ethylamine (CE6) and 2-(5-tert-Butyl-[1,3,4]oxadiazol-2-yl)-ethylamine (CE7), are prepared by an analogous procedure to intermediate CE1 using the appropriate hydrazide in step 1.

Intermediate CF1 & CG1

2-(1-Ethyl-1H-imidazol-4-yl)-ethylamine & 2-(3-Ethyl-3H-imidazol-4-yl)-ethylamine

Step 1: 2-[2-(1H-Imidazol-4-yl)-ethyl]-isoindole-1,3-dione

N-Carbethoxy phthalimide (2.45 g, 11 mmol) is added over 10 minutes to a vigorously stirred solution of histamine (1.13 g, 1.0 mmol) and $Na_2CO_3$ (1.19 g, 1.1 mmol) in water (22 ml). After 1 h the white suspension is removed by filtration, washed with ethanol and dried to afford the titled compound.

Step 2: 2-[2-(1-Ethyl-1H-imidazol-4-yl)-ethyl]-isoindole-1,3-dione & 2-[2-(3-ethyl-3H-imidazol-4-yl)-ethyl]-isoindole-1,3-dione A suspension of 2-[2-(1H-imidazol-4-yl)-ethyl]-isoindole-1,3-dione (5.0 g, 20.7 mmol) in DMF (41.5 ml) is added slowly to a stirred suspension of NaH (0.83 g of a 60% dispersion in mineral oil, 21 mmol) at 0° C. The mixture is stirred at 0° C. for 15 min followed by warming to room temperature over 45 minutes then cooling back down to 0° C. A solution of bromoethane (1.54 ml, 20.7 mmol) in DMF (10 ml) is added dropwise. The reaction is stirred at 5° C. for 30 min followed by room temperature for 24 hours. The solvent is removed and the residue is purified by chromatography on silica eluting with DCM and MeOH (1% increasing to 3%) to give a mixture of 2-[2-(1-ethyl-1H-imidazol-4-yl)-ethyl]-isoindole-1,3-dione and the regioisomer, 2-[2-(3-ethyl-3H-imidazol-4-yl)-ethyl]-isoindole-1,3-dione.

Step 3: 2-(1-Ethyl-1H-imidazol-4-yl)-ethylamine & 2-(3-Ethyl-3H-imidazol-4-yl)-ethylamine Hydrazine hydrate (0.18 ml, 3.71 mmol) is added to a stirred 70:30 mixture of 2-[2-(1-ethyl-1H-imidazol-4-yl)-ethyl]-isoindole-1,3-dione and 2-[2-(3-ethyl-3H-imidazol-4-yl)-ethyl]-isoindole-1,3-dione (1.0 g, 3.71 mmol) suspended in dry EtOH (7.4 ml) and the mixture is heated at 95° C. for 90 min. After cooling to room temperature the mixture is filtered and the solvent is removed from the filtrate to afford a mixture of the titled compounds as a yellow oil.

Intermediates CH1 & CH2

These compounds, namely 2-(2-tert-Butyl-3H-imidazol-4-yl)-ethylamine (CH1) and 2-(2-Isopropyl-3H-imidazol-4-yl)-ethylamine (CH2) are prepared according to the protocols described in R. Jain, L. A. Cohen, N. A. El-Kadi and M. M. King, *Tetrahedron* (1997), 53, pages 2365-2370.

Intermediate CI1

2-(1H-Tetrazol-5-yl)-ethylamine

This material is prepared by the protocols outlined in N. A. Delaney, G. C. Rovnyak and M. Loots, European patent specification EP 449523.

Intermediate CI2

2-(1-Ethyl-1H-tetrazol-5-yl)-ethylamine

Step 1: [2-(1-Ethyl-1H-tetrazol-5-yl)-ethyl]-carbamic acid tert-butyl ester A solution of [2-(1H-Tetrazol-5-yl)-ethyl]-carbamic acid tert-butyl ester (EP 449523) (1.0 g, 4.69 mmol) in dry THF (20 ml) is treated with a 60% dispersion of sodium hydride in mineral. oil (0.19 g, 4.69 mmol) and stirred at ambient temperature for 10 minutes. Ethyliodide (0.375 ml, 4.69 mmol) is added and the reaction mixture is heated at reflux for 7 hours, then diluted with ethylacetate and filtered. The filtrate is evaporated and the residue purified by flash silica chromatography (elution 3:2 hexanelethylacetate) to afford [2-(2-Ethyl-2H-tetrazol-5-yl)-ethyl]-carbamic acid tert-butyl ester, which elutes first, and the titled compound, [2-(1-Ethyl-1H-tetrazol-5-yl)-ethyl]-carbamic acid tert-butyl ester, which elutes next.

Step 2: 2-(1-Ethyl-1H-tetrazol-5-yl)-ethylamine

[2-(1-Ethyl-1H-tetrazol-5-yl)-ethyl]-carbamic acid tert-butyl ester (0.33 g, 1.36 imnol) is dissolved in dichloromethane (3 ml) and treated with trifluoroacetic acid (1 ml) and stirred at ambient temperature for 3 hours. The solvent is removed to afford the titled compound as the TFA salt.

Intermediate CJ1

2-(1-Ethyl-1H-tetrazol-5-yl)-ethylamine

[2-(2-Ethyl-2H-tetrazol-5-yl)-ethyl]-carbamic acid tert-butyl ester, obtained as a second product in synthesis of [2-(1-Ethyl-1H-tetrazol-5-yl)-ethyl]-carbamic acid tert-butyl ester (Intermediate CI2, step 1) is treated with TFA as described for 2-(1-Ethyl-1H-tetrazol-5-yl)-ethylamine (CI2, step 2) to afford the titled compound.

The following additional amine intermediates of formula (C)

C

Where Het. =

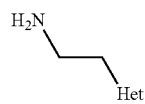

CE

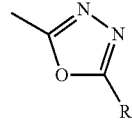

CF

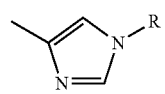

CI

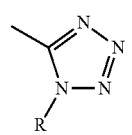

CJ

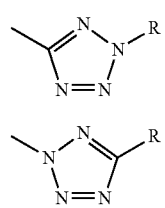

CK

-continued

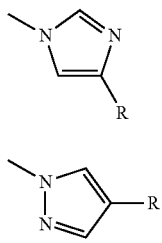

are shown in the Table 3a below, the method of preparation being described hereinafter.

TABLE 3a

| Intermediate | Het | R |
|---|---|---|
| CE8 | CE | CH₃–C(CH₃)–CH₂OH (2-hydroxymethyl-2-methyl) |
| CF2 | CF | CH₂CH₂CH₂F |
| CF3 | CF | CH₂CH₂CF₃ |
| CF4 | CF | CH₂CH₂CH(OH)CH₃ |
| CF5 | CF | (S)-CH₂CH(CH₃)CH₂OH |
| CF6 | CF | CH₂CH₂CH₂Cl |
| CI3 | CI | CH₂CH₂CH₂OH |
| CJ2 | CJ | CH₂CH₂F |
| CJ3 | CJ | CH₂CH₂CH₂OH |
| CJ4 | CJ | CH₂CH₂CH₂CH₂OH |
| CJ5 | CJ | CH(CH₃)₂ |
| CK1 | CK | CH₃ |
| CK2 | CK | cyclopropyl |
| CL1 | CL | H |
| CM1 | CM | H |
| CM2 | CM | CH₃ |

Intermediate CE8

2-[5-(2-Amino-ethyl)-[1,3,4]oxadiazol-2-yl]-2-methyl-propan-1-ol

This material is prepared by an analogous procedure to intermediate CE1 using the appropriate hydrazide in step 1.

Intermediate CF2-CF6

These compounds, namely 2-[1-(2-Fluoro-ethyl)-1H-imidazol-4-yl]-ethylamine (CF2), 2-[1-(3,3,3-Trifluoro-propyl)-1H-imidazol-4-yl]-ethylamine (CF3), 4-[4-(2-Amino-ethyl)-imidazol-1-yl]-butan-2-ol (CF4), (S)-3-[4-(2-Amino-ethyl)-imidazol-1-yl]-2-methyl-propan-1-ol (CF5) and 2-[1-(2-Chloro-ethyl)-1H-imidazol-4-yl]-ethylamine, are prepared by an analogous procedure to intermediate CF1 using the appropriate halo adduct in step 2.

Intermediate CI3

3-[5-(2-Amino-ethyl)-tetrazol-1-yl]-propan-1-ol

This material is prepared by an analogous procedure to intermediate CI2 by replacing the ethyliodide in step 1 with 3-bromo-1-propanol.

Intermediate CJ2

2-[2-(2-Fluoro-ethyl)-2H-tetrazol-5-yl]-ethylamine

Step 1 {2-[2-(2-Fluoro-ethyl)-2H-tetrazol-5-yl]-ethyl}-carbamic acid tert-butyl ester To a solution comprising [2-(1H-Tetrazol-5-yl)-ethyl]-carbamic acid tert-butyl ester (EP 449523) (0.125 g, 0.586 mmol) in DMF (5 ml) is added caesium carbonate (0.23 g, 0.703 mmol) followed by 1-bromo-2-fluoroethane (0.174 ml, 2.344 mmol) and the reaction mixture is left to stir at room temperature for 3 days. The solvent is removed in vacuo and the crude residue is purified by flash silica chromatography (elution 3:2 increasing to 1:4 hexane/ethyl acetate) to afford the titled compound and {2-[1-(2-Fluoro-ethyl)-1H-tetrazol-5-yl]-ethyl}-carbamic acid tert-butyl ester.

Step 2: 2-[2-(2-Fluoro-ethyl)-2H-tetrazol-5-yl]-ethylamine

A solution of {2-[2-(2-Fluoro-ethyl)-2H-tetrazol-5-yl]-ethyl}-carbamic acid tert-butyl ester (step 1) (0.025 g, 0.0964 mmol) in DCM (3 ml) is treated with hydrochloric acid (1 ml, 4M in dioxane) and allowed to stir at room temperature for 1 hour. The reaction mixture is concentrated in vacuo to yield the titled compound as a white solid.

Intermediate CJ3 and CJ4

These compounds namely, 2-[5-(2-Amino-ethyl)-tetrazol-2-yl]-ethanol and 3-[5-(2-Amino-ethyl)-tetrazol-2-yl]-propan-1-ol are prepared analogously to intermediate CI2 but replacing the ethyliodide in step 1 with the appropriate haloalcohol and by treating the product with 4M HCl instead of trifluoroacetic acid (step 2).

Intermediate CJ5

2-(2-Isopropyl-2H-tetrazol-5-yl)-ethylamine

This compound is prepared by an analogous procedure to intermediate CI2 by replacing the ethyliodide in step 1 with the appropriate haloalkane.

Intermediate CK1

2-(5-Methyl-tetrazol-2-yl)-ethylamine

This compound is prepared by an analogous procedure to intermediate CI2 by replacing [2-(1H-Tetrazol-5-yl)-ethyl]-carbamic acid tert-butyl ester in step 1 with 5-Methyl-2H-tetrazole and by replacing ethyliodide with (2-Bromo-ethyl)-carbamic acid tert-butyl ester.

Intermediate CK2

2-(5-Cyclopropyl-tetrazol-2-yl)-ethylamine

This compound is prepared by an analogous procedure to intermediate CK1 by replacing 5-Methyl-2H-tetrazole in step 1 with 5-Cyclopropyl-2H-tetrazole.

Intermediate CL1

2-Imidazol-1-yl-ethylamine

A mixture comprising 2-chloroethylamine hydrochloride (3.00 g, 25.86 mmol), imidazole (1.63 g, 23.94 mmol) tetrabutylammonium hydrogen sulfate (0.3 g, cat.), NaOH (3.45 g, 86.18 mmol) and acetonitrile (75 ml) is stirred at reflux (81° C.) under an inert atmosphere for 20 hrs. The reaction mixture is allowed to warm to room temperature and the suspension is filtered and the solvent is concentrated in vacuo to yield the titled compound as a pale yellow oil.

Intermediate CM1

2-Pyrazol-1-yl-ethylamine

This compound is prepared according to the protocol described in A. M. Cuadro, M. P. Matia, J. L. Garcia, J. J. Vaquero, J. Alvarez-Bailla, *Synth. Commun.* 1991, 21, p 535.

Intermediate CM2

2-(4-Methyl-pyrazol-1-yl)-ethylamine

This compound is prepared using an analogous procedure to intermediate CM1 by replacing 1H-pyrazole with 4-Methyl-1H-pyrazole.

The amine intermediates (C) that are used to prepare the compounds of Examples 121 to are commercially available or are prepared by the procedure that is analogous to that described in Example 121.

The following urea intermediates of formula (D)

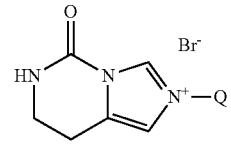

D are shown in Table 4 below, the method of preparation being described hereinafter.

TABLE 4

| Intermediate | Q |
|---|---|
| DA | —$CH_2CH_2CH_3$ |
| DB | —$CH_2CH_2CH_2CH_3$ |
| DC | —$CH(CH_3)_2$ |
| DD | —$CH_2CH(CH_3)_2$ |
| DE | —$CH_2CH_2OH$ |
| DF | —$CH_2CH_2OCH_3$ |
| DG | —$CH_2CH_2CH_2OH$ |

Intermediates DA-DG

The compounds shown in table 4, namely: 5-Oxo-2-propyl-5,6,7,8-tetrahydro-imidazo[1,5-c]pyrimidin-2-ium bromide (DA), 2-Butyl-5-oxo-5,6,7,8-tetrahydro-imidazo[1,5-c]pyrimidin-2-ium bromide (DB), 2-Isopropyl-5-oxo-5,6,7,8-tetrahydro-imidazo[1,5-c]pyrimidin-2-ium (DC), 2-Isobutyl-5-oxo-5,6,7,8-tetrahydro-imidazo[1,5-c]pyrimidin-2-ium bromide (DD), 2-(2-Hydroxy-ethyl)-5-oxo-5,6,7,8-tetrahydro-imidazo[1,5-c]pyrimidin-2-ium bromide (DE), 2-(2-Methoxy-ethyl)-5-oxo-5,6,7,8-tetrahydro-imidazo[1,5-c]pyrimidin-2-ium bromide (DF) and 2-(3-Hydroxy-propyl)-5-oxo-5,6,7,8-tetrahydro-imidazo[1,5-c]pyrimidin-2-ium (DG) are prepared by alkylation of 7,8-Dihydro-6H-imidazo[1,5-c]pyrimidin-5-one with the appropriate alkyl bromide following the method described in R. Jain and L. A. Cohen, *Tetrahedron*, (1996), 52, 5363-5370.

Preparation of Final Compounds

Compounds of formula I which are also of formula XIII

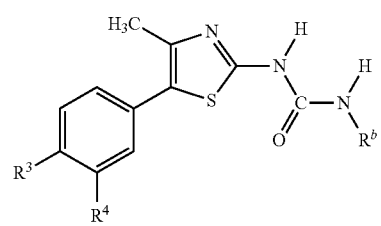

XIII are shown in Table 5 below, the method of preparation being described hereinafter. The table also shows mass spectrometry data. The Examples are in free form.

TABLE 5
| Ex. | R³ | R⁴ | Rᵇ | M/s MH+ |
|---|---|---|---|---|
| 1 | —SO₂CH₃ | F | 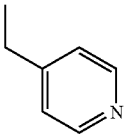 | 421.2 |
| 2 | —SO₂CH₃ | F | 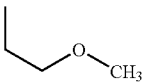 | 388.2 |
| 3 | —SO₂CH₃ | F | 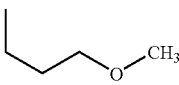 | 402.3 |
| 4 | —SO₂CH₃ | F | 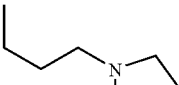 | 455.3 |
| 5 | —SO₂CH₃ | F | 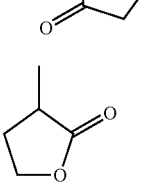 | 414.2 |
| 6 | —SO₂CH₃ | F | 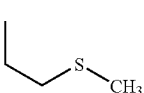 | 404.2 |
| 7 | —SO₂CH₃ | F | 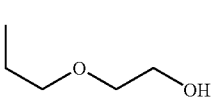 | 418.3 |
| 8 | —SO₂CH₃ | F | 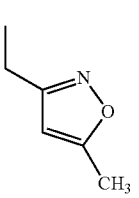 | 425.3 |
| 9 | —SO₂CH₃ | F | 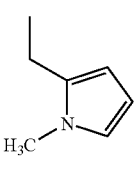 | 423.3 |
| 10 | —SO₂CH₃ | F | 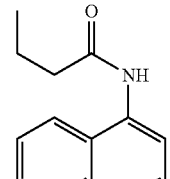 | 527.1 |
| 11 | —SO₂CH₃ | F | 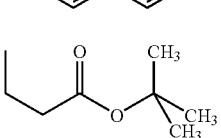 | 458.3 |
| 12 | —SO₂CH₃ | F | 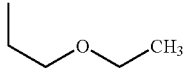 | 402.3 |
| 13 | —SO₂CH₃ | F | 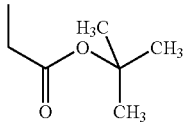 | 444.1 |
| 14 | —SO₂CH₃ | F | 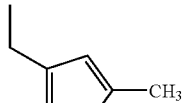 | 438.1 |
| 15 | —SO₂CH₃ | F | 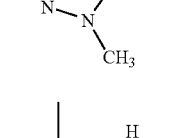 | 415.1 |
| 16 | —SO₂CH₃ | F | 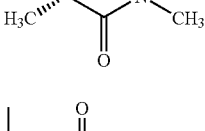 | 471.2 |
| 17 | —SO₂CH₃ | F | 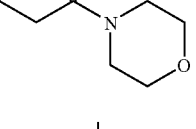 | 388.1 |
| 18 | —SO₂CH₃ | F | 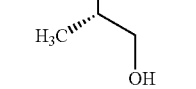 | 416.1 |
| 19 | —SO₂CH₃ | F | 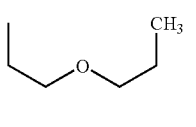 | 415.1 |
| 20 | —SO₂CH₃ | F | 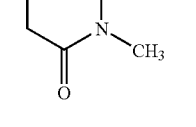 | 429.1 |
| 21 | —SO₂CH₃ | F | 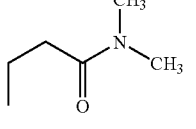 | 429.2 |
| 22 | —SO₂CH₃ | F | 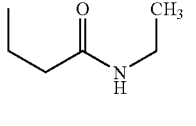 | 429.1 |

TABLE 5-continued

| Ex. | R³ | R⁴ | Rᵇ | M/s MH+ |
|---|---|---|---|---|
| 23 | —SO₂CH₃ | F | butanamide | 401.2 |
| 24 | —SO₂CH₃ | F | tert-butyl 2-methylbutanoate | 472.2 |
| 25 | —SO₂CH₃ | —CF₃ | 2-ethylpyridine | 471.1 |
| 26 | —SO₂CH₃ | —CF₃ | N-(2-(dimethylamino)ethyl)butanamide | 522.2 |
| 27 | —SO₂CH₃ | —CF₃ | 3-ethylpyridine | 471.1 |
| 28 | —SO₂CH₃ | —CF₃ | 1-methoxypropyl | 438.1 |
| 29 | —SO₂CH₃ | —CF₃ | propanol | 424.1 |
| 30 | —SO₂CH₃ | —CF₃ | pentanol | 452.1 |
| 31 | —SO₂CH₃ | —CF₃ | 4-methoxybutyl | 452.1 |
| 32 | —SO₂CH₃ | —CF₃ | 1-butyl-2-pyrrolidinone | 505.2 |
| 33 | —SO₂CH₃ | —CF₃ | N,N-diethylpropylamine | 479.2 |
| 34 | —SO₂CH₃ | —CF₃ | 4-(methylthio)butyl | 468.1 |
| 35 | —SO₂CH₃ | —CF₃ | 3-methyltetrahydrofuran-2-one | 464.1 |
| 36 | —SO₂CH₃ | —CF₃ | 1-methyl-2-propylpyrrolidine | 491.2 |
| 37 | —SO₂CH₃ | —CF₃ | 2-(propyloxy)ethanol | 468.1 |
| 38 | —SO₂CH₃ | —CF₃ | 2-ethyl-1-methylpyrrole | 473.1 |
| 39 | —SO₂CH₃ | —CF₃ | 1-morpholinobutan-1-one | 521.2 |
| 40 | —SO₂CH₃ | —CF₃ | tert-butyl butanoate | 508.2 |
| 41 | —SO₂CH₃ | —CF₃ | 1-ethoxypropyl | 452.2 |
| 42 | —SO₂CH₃ | —CF₃ | butanenitrile | 433.1 |
| 43 | —SO₂CH₃ | —CF₃ | N-methyl tropane | 503.2 |
| 44 | —SO₂CH₃ | —CF₃ | N-pentylacetamide | 493.2 |
| 45 | —SO₂CH₃ | —CF₃ | methyl 2-methylpropanoate | 466.1 |
| 46 | —SO₂CH₃ | —CF₃ | methyl (S)-2-methylpropanoate | 466.1 |

TABLE 5-continued
| Ex. | R³ | R⁴ | Rᵇ | M/s MH+ |
|---|---|---|---|---|
| 47 | —SO₂CH₃ | —CF₃ | 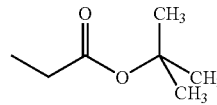 | 494.2 |
| 48 | —SO₂CH₃ | —CF₃ | 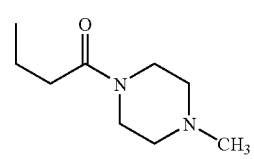 | 534.2 |
| 49 | —SO₂CH₃ | —CF₃ | 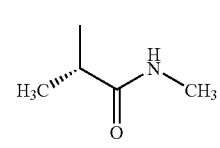 | 465.1 |
| 50 | —SO₂CH₃ | —CF₃ | 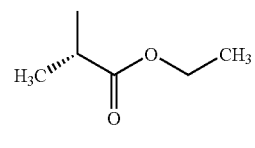 | 480.2 |
| 51 | —SO₂CH₃ | H | 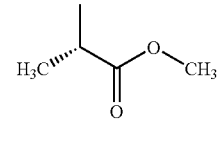 | 398.1 |
| 52 | —SO₂CH₃ | H | 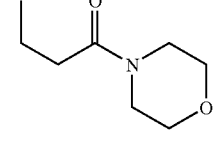 | 453.2 |
| 53 | —SO₂CH₃ | H | 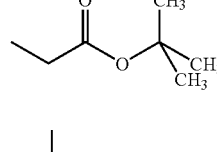 | 426.2 |
| 54 | —SO₂CH₃ | H | 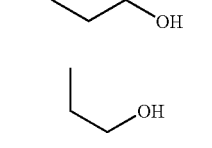 | 370.1 |
| 55 | —SO₂CH₃ | H | 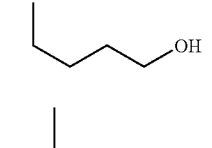 | 356.2 |
| 56 | —SO₂CH₃ | H | 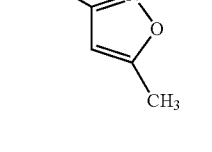 | 384.2 |
| 57 | —SO₂CH₃ | H |  | 407.2 |
| 58 | —SO₂CH₃ | H | 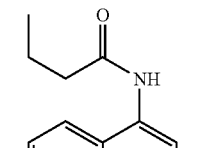 | 509.2 |
| 59 | —SO₂CH₃ | H | 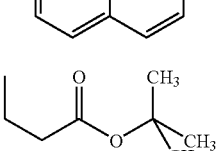 | 440.2 |
| 60 | —SO₂CH₃ | H | 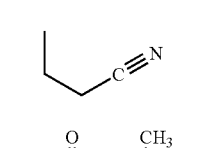 | 365.1 |
| 61 | —SO₂CH₃ | CN | 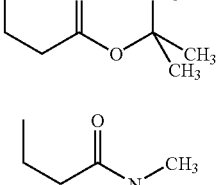 | 465.2 |
| 62 | —SO₂CH₃ | CN | 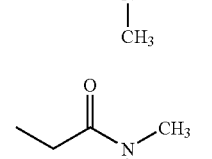 | 436.1 |
| 63 | —SO₂CH₃ | CN | 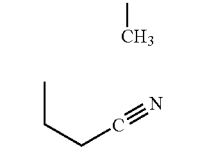 | 422.2 |
| 64 | F | —SO₂CH₃ | 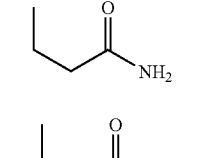 | 383 |
| 65 | F | —SO₂CH₃ | 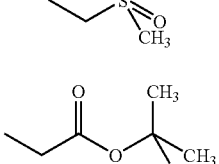 | 401 |
| 66 | F | —SO₂CH₃ | 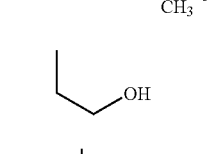 | 436 |
| 67 | F | —SO₂CH₃ | 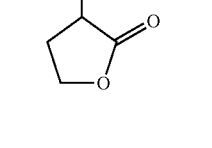 | 444 |
| 68 | F | —SO₂CH₃ | 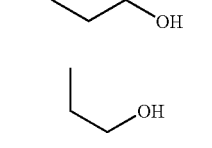 | 374 |
| 69 | F | —SO₂CH₃ |  | 414 |

TABLE 5-continued

| Ex. | R³ | R⁴ | Rᵇ | M/s MH+ |
|---|---|---|---|---|
| 70 | F | —SO₂CH₃ | 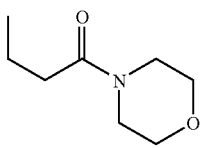 | 471 |
| 71 | —SO₂CH₃ | Cl | 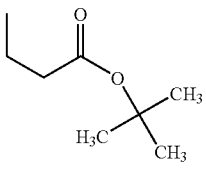 | 474.1 |
| 71a | —SO₂CH₃ | F | 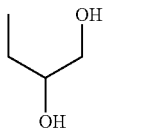 | 404.0 |

Compounds of formula I that are also of formula XIV

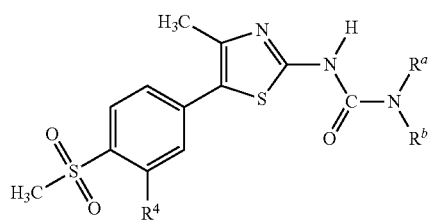

XIV are shown in Table 6 below, the method of preparation being described hereinafter. The table also shows mass spectrometry data. The Examples are in free form.

TABLE 6

$$-N\begin{matrix}R^a\\R^b\end{matrix}$$

| Ex. | R⁴ | Rᵇ | M/s MH+ |
|---|---|---|---|
| 72 | F | 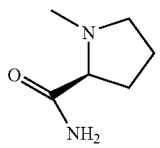 | 427.1 |
| 73 | F | 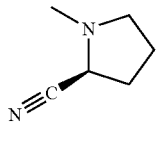 | 436.13 |
| 74 | F | 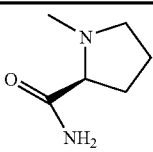 | 428.13 |

TABLE 6-continued $$-N\begin{matrix}R^a\\R^b\end{matrix}$$

| Ex. | R⁴ | Rᵇ | M/s MH+ |
|---|---|---|---|
| 75 | F | 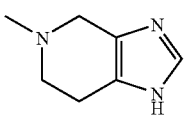 | 395.11 |
| 76 | H | 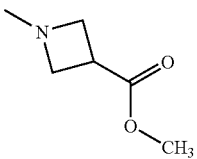 | 409.17 |
| 77 | —CF₃ | | 477.16 |
| 78 | —CF₃ | | 459.13 |
| 78a | | | 475.17 |

Compounds of formula I that are also of formula XV

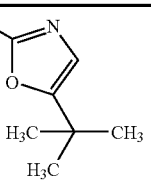

XV are shown in Table 7 below, the method of preparation being described hereinafter. The table also shows mass spectrometry data. The Examples are in free form.

TABLE 7

| Ex. | R⁴ | Het | M/s MH+ |
|---|---|---|---|
| 79 | F | | 481.1 |

TABLE 7-continued
| Ex. | R⁴ | Het | M/s MH+ |
|---|---|---|---|
| 80 | F | 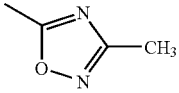 | 440.0 |
| 81 | F | 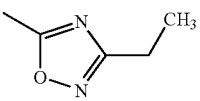 | 454.2 |
| 82 | F | 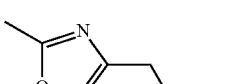 | 468.19 |
| 83 | F | 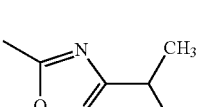 | 268.18 |
| 84 | F | 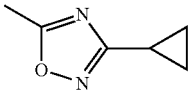 | 466.13 |
| 85 | F | 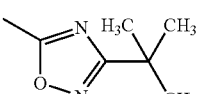 | 482.2 |
| 86 | F | 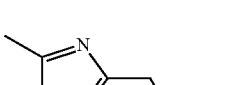 | 483.23 |
| 87 | F | 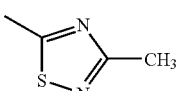 | — |
| 88 | F | 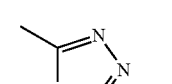 | 440.12 |
| 89 | F | 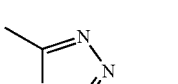 | 454.25 |
| 90 | F | 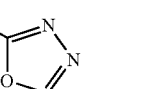 | 468.16 |
| 91 | F | 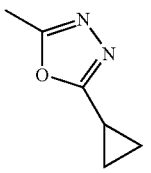 | 466.10 |
| 92 | F | 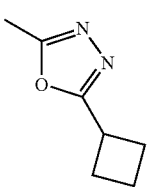 | 480.14 |
| 93 | F | 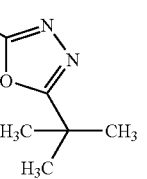 | 482.14 |
| 94 | F | 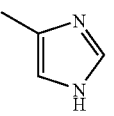 | 424.18 |
| 95 | F | 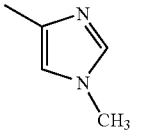 | 438.16 |
| 96 | F | 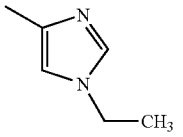 | 452.17 |
| 97 | F | 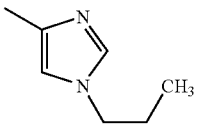 | 466.22 |
| 98 | F | 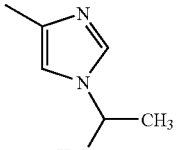 | 466.22 |
| 99 | F | 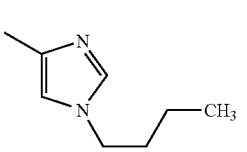 | 480.25 |

TABLE 7-continued
| Ex. | R⁴ | Het | M/s MH+ |
|---|---|---|---|
| 100 | F | 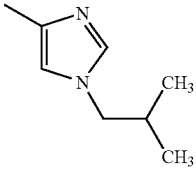 | 480.26 |
| 101 | F | 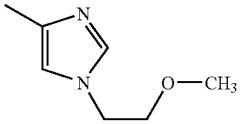 | 482.24 |
| 102 | F | 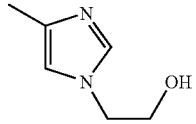 | 468.24 |
| 103 | F | 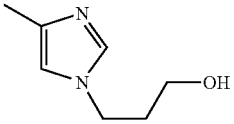 | 482.24 |
| 104 | F | 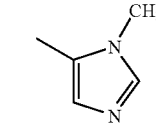 | 438.20 |
| 105 | F | 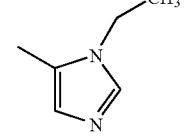 | 452.17 |
| 105a | F | 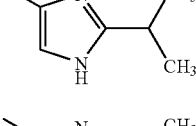 | 466.23 |
| 106 | F | 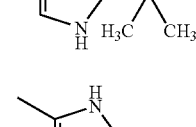 | 480.26 |
| 107 | F | 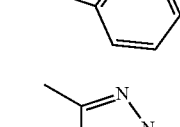 | 474.89 |
| 108 | F | 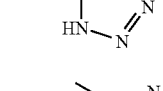 | 426.18 |
| 109 | F | 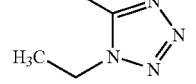 | 454.17 |
| 110 | F | 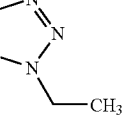 | 454.15 |
| 111 | —CF₃ | 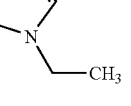 | 502.19 |
| 112 | Cl | 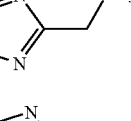 | 470.11 |
| 113 | Cl | 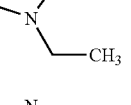 | 468.18 |
| 114 | —CN | 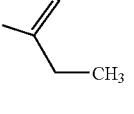 | 460.2 |
| 115 | —CN | 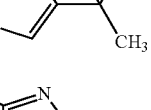 | 488.10 |
| 116 | 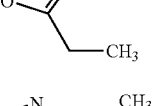 | 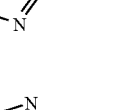 | 501.20 |
| 117 | 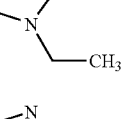 | 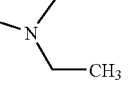 | 502.10 |
| 118 | 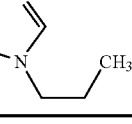 |  | 500.29 |
| 119 | —CN |  | 459.24 |
| 120 | H |  | 448.14 |

Preparation of Specific Examples:

The amines that are used to prepare the compounds of the Examples listed in Tables 5 and 6 are commercially available or prepared by standard methods. Some of the amines that are exemplified in Table 3 and are used to prepare the compounds of the Examples listed in Table 7 are not commercially available, the methods of preparation being described above. Several examples in Table 7 are prepared from intermediates that are listed in Table 4.

General Procedure for Preparation of Urea Examples from Imidazole-urea Intermediates (B) and Amines (C):

The amine (0.12 mmol) in dry DMF (0.12 mmol) is added to a solution/suspension of the imidazole urea intermediate (0.11 mmol) in DMF (1.0 ml). Triethylamine may be added to enhance reaction rate and especially if one or both of the starting materials is present as a salt (1.1 equivalents Et$_3$N per equiv. salt). The reaction mixture is sonicated if necessary until a clear solution is obtained. The reaction is allowed to proceed at between room temperature and 70° C. until the starting material is consumed (30 minutes to 24 hours). When complete, the mixture is concentrated in vacuo to remove the solvent. The product is conveniently purified by dissolving the crude residue in THF (2 ml) and adding this to polymer supported isocyanate (Argonaut Technologies, 0.5 g, 1.10 mmol) which has been pre-swollen with TBF (2 ml). The reaction mixture is allowed to drip through the resin under gravity and the solvent is removed in vacuo to yield the tided compound. Alternatively the product is purified by standard procedure e.g. crystallisation, chromatography or HPLC. A typical example is as follows:

Example 114

1-[5-(3-Cyano-4-methanesulfonyl-phenyl)-4-methyl-thiazol-2-yl]-3-[2-(5-ethyl-oxazol-2-yl)-ethyl]-urea To a stirred solution of imidazole-1-carboxylic acid [5-(3-cyano-4-methanesulfonyl-phenyl)-4-methyl-thiazol-2-yl]-amide (Intermediate BD) (0.05 g, 1.29 mmol) in DMF (1.5 ml) under an inert atmosphere is added 2-(5-ethyl-oxazol-2-yl)-ethylamine (Amine) (0.018 g, 1.29 mmol) followed by triethylamine (0.02 ml, 0.14 mmol). The reaction mixture is heated to 70° C. for 2.5 hours and then allowed to cool to room temperature. The solvent is removed in vacuo and the resulting crude residue is dissolved in THF and passed through a 0.5 g polymer supported isocyanate resin (pre-washed with THE). The solution is concentrated in vacuo and the crude residue is dissolved in DCM and washed with water, brine, dried over MgSO$_4$ and concentrated in vacuo again. Triturating with ether affords the titled compound as a yellow solid.

The compounds of Examples 97-103 are prepared from intermediates DA-DG (Table 3). A typical example is as follows:

Example 97

1-[5-(3-Fluoro-4-methanesulfonyl-phenyl)-4-methyl-thiazol-2-yl]-3-[2-(1-propyl-1H-imidazol-4-yl)-ethyl]-urea A stirred mixture of 5-oxo-2-propyl-5,6,7,8-tetrahydro-imidazo[1,5-c]pyrimidin-2-ium bromide (Intermediate DA) (0.214 g, 0.83 mmol) and 5-(3-Fluoro-4-methanesulfonyl-phenyl)-4-methyl-thiazol-2-ylamine (Intermediate AA) (0.15 g, 0.55 mmol) and Et$_3$N (0.48 ml, 3.3 mmol) is heated at 120° C. for 2 days. After cooling to room temperature the mixture is diluted with EtOAc (50 ml) and washed water followed by brine. The organic extract is dried (MgSO$_4$) and the solvent is removed to give a solid. Purification by chromatography oh silica eluting with DCM:MeOH (95:5) affords the titled compound (0.06 g, 25%).

The compounds of the all of the other Examples up to and including Example 120 are prepared analogously. These compounds are namely, from Table 5: 1-[5-(3-Fluoro-4-methanesulfonyl-phenyl)-4-methyl-thiazol-2-yl]-3-pyridin-4-ylmethyl-urea (Ex.1), 1-[5-(3-Fluoro-4-methanesulfonyl-phenyl)-4-methyl-thiazol-2-yl]-3-(2-methoxy-ethyl)-urea (Ex.2), 1-[5-(3-Fluoro-4-methanesulfonyl-phenyl)-4-methyl-thiazol-2-yl]-3-(3-methoxy-propyl)-urea (Ex.3), 1-[5-(3-Fluoro-4-methanesulfonyl-phenyl)-4-methyl-thiazol-2-yl]-3-[3-(2-oxo-pyrrolidin-1-yl)-propyl]-urea(Ex.4), 1-[5-(3-Fluoro-4-methanesulfonyl-phenyl)-4-methyl-thiazol-2-yl]-3-(2-oxo-tetrahydro-furan-3-yl)-urea (Ex.5), 1-[5-(3-Fluoro-4-methanesulfonyl-phenyl)-4-methyl-thiazol-2-yl]-3-(2-methylsulfanyl-ethyl)-urea (Ex.6), 1-[5-(3-Fluoro-4-methanesulfonyl-phenyl)-4-methyl-thiazol-2-yl]-3-[2-(2-hydroxy-ethoxy)-ethyl]-urea (Ex.7), 1-[5-(3-Fluoro-4-methanesulfonyl-phenyl)-4-methyl-thiazol-2-yl]-3-(5-methyl-isoxazol-3-ylmethyl)-urea (Ex.8), 1-[5-(3-Fluoro-4-methanesulfonyl-phenyl)-4-methyl-thiazol-2-yl]-3-(1-methyl-1H-pyrrol-2-ylmethyl)-urea, (Ex.9), 3-{3-[5-(3-Fluoro-4-methanesulfonyl-phenyl)-4-methyl-thiazol-2-yl]-ureido}-N-naphthalen-2-yl-propionamide(Ex.10), 3-{3-[5-(3-Fluoro-4-methanesulfonyl-phenyl)-4-methyl-thiazol-2-yl]-ureido}-propionic acid tert-butyl ester, (Ex.11), 1-(2-Ethoxy-ethyl)-3-[5-(3-fluoro-4-methanesulfonyl-phenyl)-4-methyl-thiazol-2-yl]-urea (Ex.12), {3-[5-(3-Fluoro-4-methanesulfonyl-phenyl)-4-methyl-thiazol-2-yl]-ureido}-acetic acid tert-butyl ester, (Ex.13), 1-(1,5-Dimethyl-1H-pyrazol-3-ylmethyl)-3-[5-(3-fluoror-4-methane-sulfonyl-phenyl)-4-methyl-thiazol-2-yl]-urea (Ex.14), (S)-2-{3-[5-(3-Fluoro-4-methanesulfonyl-phenyl)-4-methyl-thiazol-2-yl]-ureido}-N-methyl-propionamide (Ex.15), 1-[5-(3-Fluoro-4-methanesulfonyl-phenyl)-4-methyl-thiazol-2-yl]-3-(3-morpholin-4-yl-3-oxo-propyl)-urea (Ex.16), 1-[5-(3-Fluoro-4-methanesulfonyl-phenyl)-4-methyl-thiazol-2-yl]-3-((S)-2-hydroxy-1-methyl-ethyl)-urea (Ex.17), 1-[5-(3-Fluoro-4-methanesulfonyl-phenyl)-4-methyl-thiazol-2-yl]-3-(2-propoxy-ethyl)-urea (Ex.18),2-{3-[5-(3-Fluoro-4-methanesulfonyl-phenyl)-4-methyl-thiazol-2-yl]-ureido}-N,N-dimethyl-acetamide (Ex.19),3-{3-[5-(3-Fluoro-4-methanesulfonyl-phenyl)4-methyl-thiazol-2-yl]-ureido}-N,N-dimethyl-propionamide (Ex.20), N-Ethyl-3-{3-[5-(3-fluoro-4-methanesulfonyl-phenyl)-4-methyl-thiazol-2-yl]-ureido}-propionamide (Ex.21), 3-{3-[5-(3-Fluoro-4-methanesulfonyl-phenyl)-4-methyl-thiazol-2-yl]-ureido}-2,2-dimethyl-propionamide (Ex.22), 3-{3-[5-(3-Fluoro-4-methanesulfonyl-phenyl)-4-methyl-thiazol-2-yl]-ureidol}propion-amide (Ex.23), 3-{3-[5-(3-Fluoro-4-methanesulfonyl-phenyl)-4-methyl-thiazol-2-yl]-ureido}-2-methyl-propionic acid tert-butyl ester (Ex.24), 1-[5-(4-Methanesulfonyl-3-trifluoromethyl-phenyl)-4-methyl-thiazol-2-yl]-3-pyridin-2-ylmethyl-urea (Ex25), N-(2-dimethylamino-ethyl)-3-{3-[5-(4-Methanesulfonyl-3-trifluoromethyl-phenyl)-4-methyl-thiazol-2-yl]-ureido}-propion-amide (Ex.26), 1-[5-(4-Methanesulfonyl-3-trifluoromethyl-phenyl)-4-methyl-thiazol-2-yl]-3-pyridin-3-ylmethyl-urea (Ex.27), 1-[5-(4-Methanesulfonyl-3-trifluoromethyl-phenyl)-4-methyl-thiazol-2-yl]-3-(2-methoxy-ethyl)-urea (Ex.28), 1-(2-Hydroxy-ethyl)-3-[5-(4-methane-sulfonyl-3-trifluoromethyl-phenyl)-4-methyl-thiazol-2-yl]-urea (Ex.29), 1-(4-Hydroxy-butyl)-3-[5-(4-methanesulfonyl-3-trifluoromethyl-phenyl)-4-methyl-thiazol-2-yl]-urea (Ex.30), 1-[5-(4-Methanesulfonyl-3-trifluoromethyl-phenyl)-4-methyl-thiazol-2-yl]-3-(3-methoxy-propyl)-urea (Ex.31), 1-[5-(4-Methanesulfonyl-3- trifluoromethyl-phenyl)-4-methyl-thiazol-2-yl]-3-[3-(2-oxo-pyrrolidin-1-yl)-propyl]-urea (Ex.32), 1-(2-Diethylamino-ethyl)-3-[5-(4-methanesulfonyl-3-trifluoromethyl-phenyl)-4-methyl-thiazol-2-yl]-urea (Ex.33), 1-[5-(4-Methanesulfonyl-3-tri-fluoromethyl-phenyl) -4-methyl-thiazol-2-yl]-3-(3-methylsulfanyl-propyl)-urea (Ex.34), 1-[5-(4-Methanesulfonyl-3-trifluoromethyl-phenyl)-4-methyl-thiazol-2-yl]-3-(2-oxo-tetrahydro-furan-3-yl)-urea (Ex.35), 1-[5-(4-Methanesulfonyl-3-trifluoromethyl-phenyl)-4-methyl-thiazol-2-yl]-3-[2-(1-methyl-pyrrolidin-2-yl)-ethyl]-urea (Ex.36), 1-[2-(2-Hydroxy-ethoxy)-ethyl]-3-[5-(4-methanesulfonyl-3-trifluoromethyl-phenyl)-4-methyl-thiazol-2-yl]-urea (Ex.37), 1-[5-(4-Methanesulfonyl-3-trifluoromethyl-phenyl)-4-methyl-thiazol-2-yl]-3-(1-methyl-1H-pyrrol-2-ylmethyl) -urea (Ex.38), 1-[5-(4-Methanesulfonyl-3-trifluoromethyl-phenyl)-4-methyl-thiazol-2-yl]-3-(3-morpholin-4-yl-3-oxo-propyl)-urea (Ex.39), 3-{3-[5-(4-Methanesulfonyl-3-trifluoro-methyl-phenyl)-4-methyl-thiazol-2-yl]-ureido)-propionic acid tert-butyl ester (Ex.40), 1-(2-Ethoxy-ethyl)-3-[5-(4-methanesulfonyl-3-trifluoromethyl-phenyl)-4-methyl-thiazol-2-yl]-urea (Ex.41), 1-(2-Cyano-ethyl)-3-[5-(4-methanesulfonyl-3-trifluoromethyl-phenyl)-4-methyl-thiazol-2-yl]-urea (Ex.41), 1-[5-(4-Methanesulfonyl-3-trifluoromethyl-phenyl)-4-methyl-thiazol-2-yl]-3-(8-methyl-8-aza-bicyclo[3.2.1]oct-3-yl)-urea (Ex.43), N-(4-{3-[5-(4-Methane-sulfonyl-3-trifluoromethyl-phenyl)-4-methyl-thiazol-2-yl]-ureido}-butyl)-acetamide (Ex.44), (R)-2-{3-[5-(4-Methanesulfonyl-3-trifluoromethyl-phenyl)-4-methyl-thiazol-2-yl]-ureido}-propionic acid methyl ester (Ex.45), (S)-2-{3-[5-(4-Methanesulfonyl-3-trifluoromethyl-phenyl)-4-methyl-thiazol-2-yl]-ureido}-propionic acid methyl ester (Ex.46), {3-[5-(4-Methanesulfonyl-3-trifluoromethyl-phenyl)4methyl-thiazol-2-yl]-ureido)-acetic acid tert-butyl ester (Ex.47), 1-[5-(4-Methanesulfonyl-3-trifluoromethyl-phenyl)-4-methyl-thiazol-2-yl]-3-[3-(4-methyl-piperazin-1-yl)-3-oxo-propyl]-urea (Ex.48), (S)-2-{3-[5-(4-Methanesulfonyl-3-trifluoromethyl-phenyl) -4-methyl-thiazol-2-yl]-ureido}-N-methyl-propionamide (Ex.49), (S)-2-{3-[5-(4-Methanesuafonyl-3-trifluoromethyl-phenyl)-4-methyl-thiazol-2-yl]-ureido}-propionic acid ethyl ester (Ex.50), (S)-2-}3-[5-(4-Methanesulfonyl-phenyl)-4-methyl-thiazol-2-yl]-ureido}-propionic acid methyl ester (Ex.51), 1-[5-(4-Methanesulfonyl-phenyl)-4-methyl-thiazol-2-yl]-3-(3-morpholin-4-yl-3-oxo-propyl)-urea (Ex.52), {3-[5-(4-Methanesulfonyl-phenyl)-4-methyl-thiazol-2-yl]-ureido}-acetic acid tert-butyl ester (Ex.53), 1-(3-Hydroxy-propyl)-3-[5-(4-methanesulfonyl-phenyl)4-methyl-thiazol-2-yl]-urea (Ex.54), 1-(2-Hydroxy-ethyl)-3-[5-(4-methanesulfonyl-phenyl)-4-methyl-thiazol-2-yl]-urea (Ex.55), 1-(4-Hydroxy-butyl)-3-[5-(4-methanesulfonyl-phenyl)-4-methyl-thiazol-2-yl]-urea (Ex.56), 1-[5-(4-Methanesulfonyl-phenyl)-4-methyl-thiazol-2-yl]-3-(5-methyl-isoxazol-3-ylmethyl)-urea (Ex.58), 3-{3-[5-(4-Methane-sulfonyl-phenyl)-4-methyl-thiazol-2-yl]-ureido}-N-naphthalen-2-yl-propionamide (Ex.58), 3-{3-[5-(4-Methanesulfonyl-phenyl)-4-methyl-thiazol-2-yl]-ureido}-propionic acid tert-butyl ester (Ex.59), 1-(2-Cyano-ethyl)-3-[5-(4-methanesulfonyl-phenyl)-4-methyl-thiazol-2-yl]-urea (Ex.60), 3-{3-[5-(3-Cyano-4-methanesulfonyl-phenyl)-4-methyl-thiazol-2-yl]ureido}-propionic acid tert-butyl ester (Ex.61), 3-{3-[5-(3-Cyano-4-methanesulfonyl-phenyl)-4-methyl-thiazol-2-yl]-ureido}-N,N-dimethyl-propionamide (Ex.62), 2-{3-[5-(3-Cyano-4-methanesulfonyl-phenyl)-4-methyl-thiazol-2-yl]-ureido}-N,N-dimethyl-acetamide (Ex.63), 1-(2-Cyano-ethyl)-3-[5-(4-fluoro-3-methanesulfonyl-phenyl)-4-methyl-thiazol-2-yl]-urea (Ex.64), 3-{3-[5-(4-Fluoro-3-methanesulfonyl-phenyl)-4-methyl-thiazol-2-yl]-ureido}-propionamide (Ex.65), 1-[5-(4-Fluoro-3-methanesulfonyl-phenyl)-4methyl-thiazol-2-yl]-3-(2-methanesulfonyl-ethyl)-urea (Ex.66), {3-[5-(4-Fluoro-3-methanesulfonyl-phenyl)-4-methyl-thiazol-2-yl]-ureido}-acetic acid tert-butyl ester (Ex.67), 1-[5-(4-Fluoro-3-methanesulfonyl-phenyl)4-methyl-thiazol-2-yl]-3-(2-hydroxy-ethyl)-urea (Ex.68), 1-[5-(4-Fluoro-3-methanesulfonyl-phenyl)-4methyl-thiazol-2-yl]-3-(2-oxo-tetrahydro-furan-3-yl)-urea (Ex.69), 1-[5-(4-Fluoro-3-methanesulfonyl-phenyl)-4-methyl-thiazol-2-yl]-3-(3-morpholin-4-yl-3-oxo-propyl)-urea (Ex.70), 3-{3-[5-(3-Chloro-4-methane-sulfonyl-phenyl)-4-methyl-thiazol-2-yl]-ureido}-propionic acid tert-butyl ester (Ex.71), and 1-(2,3-Dihydroxy-propyl)-3-[5-(3-fluoro-4-methanesulfonyl-phenyl)-4-methyl-thiazol-2-yl]-urea (Ex. 71a); from Table 6: Pyrrolidine-1,2-dicarboxylic acid 2-amide 1-{[5-(3-fluoro-4-methane-sulfonyl-phenyl)4-methyl-thiazol-2-yl]-amide} (Ex.72), 1,4,6,7-Tetrahydro-imidazo[4,5-c]-pyridine-5-carboxylic add [5-(3-fluoror-4-methanesulfonyl-phenyl)-4-methyl-thiazol-2-yl]-amide (Ex.73), 1-[5-(3-Fluoro-4-methane-sulfonyl-phenyl)-4-methyl-thiazol-2-ylcarbamoyl]-azetidine-3-carboxylic add methyl ester (Ex.74), 3-Cyano-azetidine-1-carboxylic acid [5-(3-fluoro-4-methanesulfonyl-phenyl)-4-methyl-thiazol-2-yl]-amide (Ex.75), Pyrrolidine-1,2-dicarboxylic acid 2-amide 1-{[5-(4-methanesulfonyl-phenyl)-4-methyl-thiazol-2-yl]-amide} (Ex.76), 1-(2-Hydroxy-ethyl)-3-[5-(4-methanesulfonyl-3-trifluoromethyl-phenyl)-4-methyl-thiazol-2-yl]-1-methyl-urea (Ex.77), 2-Cyano-pyrrolidine-1-carboxylic acid [5-(4-methane-sulfonyl-3-trifluoromethyl-phenyl)-4-methyl-thiazol-2-yl]-amide (Ex.78) and (S)-Pyrrolidine-1,2-dicarboxylic acid 2-amide 1-{[5-(3-imidazol-1-yl-4-methanesulfonyl-phenyl)-4-methyl-thiazol-2-yl]-amide} (Ex.78a); and from Table 7: 1-[2-(5-tert-Butyl-oxazol-2-yl)-ethyl]-3-[5-(3-fluoro-4-methanesulfonyl-phenyl)-4-methyl-thiazol-2-yl]-urea (Ex.79), 1-[5-(3-Fluoro-4-methanesulfonyl-phenyl)4-methyl-thiazol-2-yl]-3-[2-(3-methyl-[1,2,4]oxaciazol-5-yl)-ethyl]-urea (Ex.80), 1-[2-(3-Ethyl-[1,2,4]oxadiazol-5-yl)-ethyl]-3-[5-(3-fluoro-4-methanesulfonyl-phenyl)-4-methyl-thiazol-2-yl]-urea (Ex.81), 1-[2-(3-Ethyl-[1,2,4]oxadiazol-5-yl)-ethyl]-3-[5-(3-fluoro-4-methanesulfonyl-phenyl)-4-methyl-thiazol-2-yl]-urea (Ex.82), 1-[5-(3-Fluoro-4-methanesulfonyl-phenyl)4-methyl-thiazol-2-yl]-3-[2-(3-isopropyl-[1,2,4]oxadiazol-5-yl)-ethyl]-urea (Ex.83), 1-[2-(3-Cyclopropyl-[1,2,4]oxadiazol-5-yl)-ethyl]-3-[5-(3-fluoro-4-methane-sulfonyl-phenyl)4-methyl-thiazol-2-yl]-urea (Ex.84), 1-[2-(3-tert-Butyl-[1,2,4]oxadiazol-5-yl)-ethyl]-3-[5-(3-fluoro-4-methanesulfonyl-phenyl)-4-methyl-thiazol-2-yl]-urea (Ex.85), 1-[2-(3-Dimethylaminomethyl-[1,2,4]oxadiazol-5-yl)-ethyl]-3-[5-(3-fluoro-4-methanesulfonyl-phenyl)-4-methyl-thiazol-2-yl]-urea (Ex.86), 1-[5-(3-Fluoro-4-methanesulfonyl-phenyl)-4-methyl-thiazol-2-yl]-3-[2-(3-methyl-[1,2,4]thiadiazol-5-yl)-ethyl]-urea (Ex.87), 1-[5-(3-Fluoro-4-methanesulfonyl-phenyl)-4-methyl-thiazol-2-yl]-3-[2-(5-methyl-[1,3,4]oxadiazol-2-yl)-ethyl]-urea (Ex.88), 1-[2-(5-Ethyl-[1,3,4]oxadiazol-2-yl)-ethyl]-3-[5-(3-fluoro-4-methanesulfonyl-phenyl)-4-methyl-thiazol-2-yl]-urea (Ex.89), 1-[5-(3-Fluoro-4-methanesulfonyl-phenyl)-4-methyl-thiazol-2-yl]-3-[2-(5-isopropyl-[1,3,4]oxadiazol-2-yl)-ethyl]-urea (Ex.90), 1-[2-(5-Cydopropyl-[1,3,4]oxadiazol-2-yl)-ethyl]-3-[5-(3-fluoro-4-methane-sulfonyl-phenyl)-4-methyl-thiazol-2-yl]-urea (Ex.91), 1-[2-(5-Cyclo-butyl-[1,3,4]oxadiazol-2-yl)-ethyl]-3-[5-(3-fluoro-4-methanesulfonyl-phenyl)-4-methyl-thiazol-2-yl]-urea (Ex.92), 1-[2-(5-tert-Butyl-[1,3,4]oxa-diazol-2-yl)-ethyl]-3-[5-(3-fluoro-4-methane-sulfonyl-phenyl)-4-methyl-thiazol-2-yl]-urea (Ex.93), 1-[5-(3-Fluoro-4-methanesulfonyl-phenyl)-4-methyl-thiazol-2-yl]-3-[2-(1H-imidazol-4-yl)-ethyl]urea (Ex.94), 1-[5-(3-Fluoro-4-methanesulfonyl-phenyl)-4-methyl-thiazol-2-yl]-3-[2-(1-methyl-1H-imidazol-4-yl)-ethyl]-urea (Ex.95), 1-[2-(1-Ethyl-1H-imidazol4-yl)-ethyl]-3-[5-(3-fluoro-4-methanesulfonyl-phenyl)-4-methyl-thiazol-2-yl]-urea (Ex.96), 1-[5-(3-Fluoro-4-methanesulfonyl-phenyl)-4-methyl-thiazol-2-yl]-3-[2-(1-propyl-1H-imidazol-4-yl)-ethyl]-urea (Ex.97), 1-[5-(3-Fluoro-4-methanesulfonyl-phenyl)-4- methyl-thiazol-2-yl]-3-[2-(1-isopropyl-1H-imidazol-4-yl)-ethyl]-urea (Ex.98), 1-[2-(1-Butyl-1H-imidazol-4-yl)-ethyl]-3-[5-(3-fluoro-4-methanesulfonyl-phenyl)-4-methyl-thiazol-2-yl]-urea (Ex.99), 1-[5-(3-Fluoro-4-methane-sulfonyl-phenyl) -4-methyl-thiazol-2-yl]-3-[2-(1-isobutyl-1H-imidazol-4-yl)-ethyl]-urea (Ex.100), 1-[5-(3-Fluoro-4-methanesulfonyl-phenyl)-4-methyl-thiazol-2-yl]-3-{2-[1-(2-methoxy-ethyl) -1H-imidazolyl-4-yl]-ethyl}-urea (Ex.101), 1-[5-(3-Fluoro-4-methanesulfonyl-phenyl)-4-methyl-thiazol-2-yl]-3-{2-[1-(2-hydroxy-ethyl)-1H-imidazol-4-yl]-ethyl}urea (Ex.102), 1-[5-(3-Fluoro-4-methanesulfonyl-phenyl)4-methyl-thiazol-2-yl]-3-{2-[1-(3-hydroxy-propyl)-1H-imidazol-4-yl]-ethyl}-urea (Ex.103), 1-[5-(3-Fluoro-4-methanesulfonyl-phenyl)-4-methyl-thiazol-2-yl]-3-[2-(3-methyl-3H-imidazol-4-yl)-ethyl]-urea (Ex.104), 1-[2-(3-Ethyl-3H -imidazol-4-yl)-ethyl]-3-[5-(3-fluoro-4-methanesulfonyl-phenyl)-4-methyl-thiazol-2-yl]-urea (Ex.105), 1-[5-(3-Fluoro-4-methanesulfonyl-phenyl)-4-methyl-thiazol-2-yl]-3-[2-(2-isopropyl-3H-imidazol-4-yl)-ethyl]-urea (Ex.105a), 1-[2-(2-tert-Butyl-1H-imidazol-4-yl)-ethyl]-3-[5-(3-fluoro-4-methanesulfonyl-phenyl)-4-methyl-thiazol-2-yl]-urea (Ex.106), 1-[2-(1H-Benzo-imidazol-2-yl)-ethyl]-3-[5-(3-fluoro-4-methanesulfonyl-phenyl)-4-methyl-thiazol-2-yl]-urea (Ex.107), 1-[5-(3-Fluoro-4-methanesulfonyl-phenyl)-4-methyl-thiazol-2-yl]-3-[2-(1H-tetrazol-5-yl)-ethyl]urea (Ex.108), 1-[2-(1-Ethyl-1H-tetrazol-5-yl)-ethyl]-3-[5-(3-fluoro-4-methane-sulfonyl-phenyl)-4-methyl-thiazol-2-yl]-urea (Ex.109), 1-[2-(2-Ethyl-2H-tetrazol-5-yl)-ethyl]-3-[5-(3-fluoro-4-methanesulfonyl-phenyl)-4-methyl-thiazol-2-yl]-urea (Ex.110), 1-[2-(1-Ethyl-1H-imidazol-4-yl)-ethyl]-3-[5-(4-methanesulfonyl-3-trifluoro-methyl-phenyl)-4-methyl-thiazol-2-yl]-urea (Ex.111), 1-[5-(3-Chloro-4-methanesulfonyl-phenyl)-4-methyl-thiazol-2-yl]-3-[2-(3-ethyl-[1,2,4]oxadiazol-5-yl)-ethyl]-urea (Ex.112), 1-[5-(3-Chloro-4-methanesulfonyl-phenyl)4-methyl-thiazol-2-yl]-3-[2-(1-ethyl-1H-imidazol-4-yl)-ethyl]-urea (Ex.113), 1-[5-(3-Cyano-4-methanesulfonyl-phenyl)-4-methyl-thiazol-2-yl]-3-[2-(5-ethyl-oxazol-2-yl)-ethyl]-urea (Ex.114), 1-[2-(5-tert-Butyl-oxazol-2-yl)-ethyl]-3-[5-(3-cyano-4-methanesulfonyl-phenyl)-4-methyl-thiazol-2-yl]-urea (Ex.115), 1-[2-(5-Ethyl-oxazol-2-yl)-ethyl]-3-[5-(3-imidazol-1-yl-4-methane-sulfonyl-phenyl) -4-methyl-thiazol-2-yl]-urea (Ex.116), 1-[2-(3-Ethyl-[1,2,4]oxadiazol-5-yl) -ethyl]-3-[5-(3-imidazol-1-yl-4-methanesulfonyl-phenyl)-4-methyl-thiazol-2-yl]-urea (Ex.117) 1-[2-(1-Ethyl-1H-imidazol-4-yl)-ethyl]-3-[5-(3-imidazol-1-yl-4-methane-sulfonyl-phenyl)-4-methyl-thiazol-2-yl]-urea (Ex.118), 1-[5-(3-Cyano-4-methane-sulfonyl-phenyl)-4-methyl-thiazol-2-yl]-3-[2-(1-ethyl-1H-imidazol-4-yl)-ethyl]-urea (Ex.119), and 1-[5-(4-Methane-sulfonyl-phenyl) -4-methyl-thiazol-2-yl]-3-[2-(1-propyl-1H-imidazol-4-yl)-ethyl]-urea (Ex.120).

Compounds of formula I that are also of formula XVI

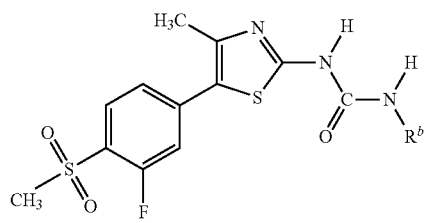

XVI are shown in Table 8 below, the method of preparation being described hereinafter. The table also shows mass spectrometry data. The Examples are in free form.

TABLE 8

| Ex. | $R^b$ | M/s MH+ |
|---|---|---|
| 121 | butyryl-NH-CH(CH₃)₂ (N-isopropylbutyramide) | 457.1 |
| 122 | CH₃CH₂-O-CH(OCH₂CH₃)-(CH₂)₃- (1,1-diethoxypentyl) | 474.2 |
| 123 | CH₃-O-CH(OCH₃)-(CH₂)₃- (1,1-dimethoxypentyl) | 446.2 |
| 124 | 5-ethyl-1H-tetrazol-yl | 412.1 |
| 125 | butyryl-NH-CH₂-C(CH₃)₃ (N-neopentylbutyramide) | 471.2 |
| 126 | butyryl-NH-CH₃ (N-methylbutyramide) | 415.1 |
| 127 | butyryl-N(CH₃)-CH₂-CH(CH₃)₂ (N-isobutyl-N-methylbutyramide) | 471.2 |
| 128 | butyryl-N(CH₃)-CH(CH₃)₂ (N-isopropyl-N-methylbutyramide) | 457.2 |
| 129 | butyryl-NH-CH₂-C(CH₃)₂-CH₂-N(CH₃)₂ | 514.2 |
| 130 | propionyl-NH-C(CH₃)₂-CH₂CH₃ (N-tert-amylpropionamide) | 443.2 |
| 131 | 5-ethyl-2-ethyl-2H-tetrazol-yl | 440.2 |
| 132 | 5-ethyl-1-ethyl-1H-tetrazol-yl | 440.2 |

TABLE 8-continued

| Ex. | R$^b$ | M/s MH+ |
|---|---|---|
| 133 | [propionamide, N-(2-methylbutan-2-yl)] | 457.2 |
| 134 | [N-methyl-N-propyl propionamide] | 443.2 |
| 135 | [N-propyl propionamide] | 429.2 |
| 136 | [N-neopentyl propionamide] | 457.2 |
| 137 | [N-tert-butyl-N-methyl propionamide] | 457.1 |
| 138 | [N-isopropyl-N-methyl propionamide] | 443.1 |
| 139 | [1-morpholinopropan-1-one] | 457.0 |
| 140 | [N-ethyl-N-methyl propionamide] | 429.0 |
| 141 | [2-ethyl-5-isopropyl-1,3,4-oxadiazole] | 454.2 |
| 142 | [N-(3-(dimethylamino)-2,2-dimethylpropyl) propionamide] | 500.2 |
| 143 | [N-isobutyl-N-methyl propionamide] | 457.2 |

TABLE 8-continued

| Ex. | R$^b$ | M/s MH+ |
|---|---|---|
| 144 | [2,5-diethyl-1,3,4-oxadiazole] | 440.1 |
| 145 | [N-(2-methylbutan-2-yl) butyramide] | 471.2 |
| 146 | [N-(3-(dimethylamino)-2,2-dimethylpropyl) butyramide] | 500.2 |
| 147 | [1-(4,4-dimethyloxazolidin-3-yl) butan-1-one] | 485.3 |
| 148 | [2-propyl-5-methyl-tetrazole] | 440.2 |
| 149 | [2-propyl-5-cyclopropyl-tetrazole] | 466.1 |
| 150 | [2-isopropyl-5-propyl-tetrazole] | 468.1 |
| 151 | [1-propyl-imidazole] | 424.1 |
| 152 | [1-((S)-2-methyl-3-hydroxypropyl)-5-propyl-imidazole] | 496.2 |
| 153 | [1-(3-hydroxybutyl)-4-propyl-imidazole] | 496.2 |

TABLE 8-continued

| Ex. | $R^b$ | M/s MH+ |
|---|---|---|
| 154 | 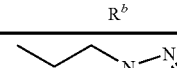 | 438.1 |

Example 121

N-tert-Butyl-3-{3-[5-(3-fluoro-4-methanesulfonyl-phenyl)-4-methyl-thiazol-2-yl]-ureido}-propionamide

Step 1: (2-tert-Butylcarbamoyl-ethyl)-carbamic acid tert-butyl ester

A solution of 3-tert-Butoxycarbonylamino-propionic acid (0.5 g, 2.64 mmol) in DCM (5 ml) under an inert atmosphere is treated with 1-hydroxy-7-azabenzatriazole (0.108 g, 0.79 mmol) followed by water soluble carbodiimide (0.491 g, 3.17 mnol) and tert-butylamine (0.305 ml, 2.91 mmol). The reaction mixture is stirred at room temperature for 3 hours and then citric acid (10 ml, 0.5 M) is added to the solution and extracted with DCM (2×10 ml). The combined organic layers are washed with brine (10 ml) and dried over $MgSO_4$. After filtration, the solvent is removed in vacuo to yield the titled compound as an oil.

Step2: 3-Amino-N-tert-butyl-propionamide (2-tert-Butylcarbamoyl-ethyl)-carbamic acid tert-butyl ester (0.65 g, 2.64 mmol) is dissolved in trifluoroacetic acid (3.5 ml) and allowed to stir at room temperature under an inert atmosphere for 3 hours. The solvent is removed in vacuo to yield the titled compound as a TFA salt which is used crude in the next step:

Step 3: N-tert-Butyl-3-{3-[5-(3-fluoro-4-methane-sulfonyl-phenyl)-4-methyl-thiazol-2-yl]-ureido}-propionamide To a stirred solution of 3-amino-N-tert-butyl-propionamide (0.075 g, 0.29 mmol) (step 2) in DMF (2 ml) is added triethylamine (0.092 ml, 0.66 mmol) followed by imidazole-1-carboxylic acid [5-(3-fluoromethanesulfonyl-phenyl)-4-methyl-thiazol-2-yl]-amide (0.1 g, 0.26 mmol). After stirring at room temperature over night, the solvent is removed in vacuo and the residue is dissolved in ethyl acetate (10 ml). This organic portion is washed with water (2×10 ml), brine (1×10 ml). After drying ($MgSO_4$) the mixture is absorbed on silica and purified by chromatography, eluting with ethyl acetate to give the titled compound.

The compounds of Examples 122 to 154 are prepared analogously using the general procedure for preparation of urea examples from imidazole-urea intermediates (B) and amines (C) that is detailed above.

These compounds of Examples 122 to 154 are namely, 1-(4,4-Diethoxy-butyl)-3-[5-(3-fluoro-4methanesulfonyl-phenyl)-4-methyl-thiazol-2-yl]-urea (Ex.122), 1-(4,4-Dimethoxy-butyl)-3-[5-(3-fluoro-4-methanesulfonyl-phenyl)-4-methyl-thiazol-2-yl]-urea (Ex.123), 1-[5-(3-Fluoro-4-methanesulfonyl-phenyl)-4-methyl-thiazol-2-yl]-3-(1H-tetrazol-5-ylmethyl)-urea (Ex.124), N-(2,2-Dimethy-propyl)-3-{3-[5-(3-fluoro-4-methanesulfonyl-phenyl)4-methyl-thiazol-2-yl]-ureido}propionamide (Ex.125), 3-{3-[5-(3-Fluoro-4-methanesulfonyl-phenyl)-4-methyl-thiazol-2-yl]-ureido)-N-methyl-propionamide (Ex.126), 3-{3-[5-(3-Fluoro-4-methanesulfonyl-phenyl)-4-methyl-thiazol-2-yl]-ureido}-N-isobutyl-N-methyl-propionamide (Ex.127), 3-{3-[5-(3-Fluoro-4-methanesulfonyl-phenyl)-4-methyl-thiazol-2-yl]-ureido}-N-isopropyl-N-methyl-propionamide (Ex.128), N-(3-Dimethylamino-2,2-dimethyl-propyl)-3-{3-[5-(3-fluoro-4-methanesulfonyl-phenyl) -4-methyl-thiazol-2-yl]-ureido)-propionamide (Ex.129), N-tert-Butyl-2-{3-[5-(3-fluoro-4-methanesulfonyl-phenyl)-4-methyl-thiazol-2-yl]-ureido}-acetamide (Ex.130), 1-(2-Ethyl-2H-tetrazol-5-ylmethyl)-3-[5-(3-fluoro-4-methanesulfonyl-phenyl)-4-methyl-thiazol-2-yl]-urea (Ex.131), 1-(1-Ethyl-1H-tetrazol-5-ylmethyl)-3-[5-(3-fluoro-4-methanesulfonyl-phenyl)-4-methyl-thiazol-2-yl]-urea (Ex.132), N-(1,1-Dimethyl-propyl)-2-{3-[5-(3-fluoro-4-methane-sulfonyl-phenyl)-4-methyl-thiazol-2-yl]-ureido}-acetamide (Ex.133), 2-{3-[5-(3-Fluoro-4-methanesulfonyl-phenyl)4-methyl-thiazol-2-yl]-ureido}-N-methyl-N-propyl-acetamide (Ex.134), 2-{3-[5-(3-Fluoro-4-methanesulfonyl-phenyl)-4-methyl-thiazol-2-yl]-ureido}N -propyl-acetamide (Ex.135), N-(2,2-Dimethyl-propyl)-2-{3-[5-(3-fluoro-4-methanesulfonyl-phenyl) -4-methyl-thiazol-2-yl]-ureido}-acetamide (Ex.136), N-tert-Butyl-2-}3-[5-(3-fluoro-4-methanesulfonyl-phenyl)-4-methyl-thiazol-2-yl]-ureido}-N-methyl-acetamide (Ex.137), 2-{3-[5-(3-Fluoro-4-methanesulfonyl-phenyl)-4-methyl-thiazol-2-yl]-ureido)-N-isopropyl-N-methyl-acetamide (Ex.138), 1-[5-(3-Fluoro-4-methanesulfonyl-phenyl)-4-methyl-thiazol-2-yl]-3-(2-morpholin-4-yl-2-oxo-ethyl)-urea (Ex.139), N-Ethyl-2-{3-[5-(3-fluoro-4-methanesulfonyl-phenyl) -4-methyl-thiazol-2-yl]-ureido}-N-methyl-acetamide (Ex.140), 1-[5-(3-Fluoro-4-methanesulfonyl-phenyl)-4-methyl-thiazol-2-yl]-3-(5-isopropyl-[1,3,4]oxadiazol-2-ylmethyl)-urea (Ex.141), N-(3-Dimethylamino-2,2-dimethyl-propyl)-2-{3-[5-(3-fluoro-4-methanesulfonyl-phenyl) -4methyl-thiazol-2-yl]-ureido}-acetamide (Ex.142), 2-{3-[5-(3-Fluoro-4-methane-sulfonyl-phenyl) -4-methyl-thiazol-2-yl]-ureido}-N-isobutyl-N-methyl-acetamide (Ex.143), 1-(5-Ethyl-[1,3,4]oxadiazol-2-ylmethyl)-3-[5-(3-fluoro-4-methanesulfonyl-phenyl)-4-methyl-thiazol-2-yl]-urea (Ex.144), N-(1,1-Dimethyl-propyl)-3-{3-[5-(3-fluoro-4-methanesulfonyl-phenyl)-4-methyl-thiazol-2-yl]-ureido}-propionamide (Ex.145), N-(2-Dimethylamino-1,1-dimethyl-ethyl)-3-(3-[5-(3-fluoro-4-methanesulfonyl-phenyl)-4-methyl-thiazol-2-yl]-ureido}-propionamide (Ex.146), 1-[3-(4,4-Dimethyl-oxazolidin-3-yl)-3-oxo-propyl]-3-[5-(3-fluoro-4-methanesulfonyl-phenyl) -4-methyl-thiazol-2-yl]-urea (Ex.147), 1-[5-(3-Fluoro-4-methanesulfonyl-phenyl)-4-methyl-thiazol-2-yl]-3-[2-(5-methyl-tetrazol-2-yl)-ethyl]-urea (Ex.148), 1-[2-(5-Cyclopropyl-tetrazol-2-yl)-ethyl]-3-[5-(3-fluoro-4-methanesulfonyl-phenyl)-4-methyl-thiazol-2-yl]-urea (Ex.149), 1-[5-(3-Fluoro-4-methanesulfonyl-phenyl)-4-methyl-thiazol-2-yl]-3-[2-(2-isopropyl-2H-tetrazol-5-yl)-ethyl]-urea (Ex.150), 1-[5-(3-Fluoro-4-methanesulfonyl-phenyl)-4-methyl-thiazol-2-yl]-3-(2-imidazol-1-yl-ethyl)-urea (Ex.151), 1-[5-(3-Fluoro-4-methanesulfonyl-phenyl) -4-methyl-thiazol-2-yl]-3-{2-[1-((S)-3-hydroxy-2-methyl-propyl)-1H-imidazolyl]-4-yl]-ethyl}urea (Ex.152), 1-[5-(3-Fluoro-4-methanesulfonyl-phenyl)-4-methyl-thiazol-2-yl]-3-{2-[1-(3-hydroxy-butyl)-1H-imidazol-4-yl]-ethyl}-urea (Ex.153), and 1-[5-(3-Fluoro-4-methane-sulfonyl-phen-yl)-4-methyl-thiazol-2-yl]-3-[2-(4-methyl-pyrazol-1-yl)-ethyl]-urea (Ex.154).

The invention claimed is:

1. A compound which is 1-[2-(2-ethyl-2H-tetrazol-5-yl)-ethyl]-3-[5-(3-fluoro-4-methanesulfonyl-phenyl)-4-methyl-thiazol-2-yl]urea in free or salt form.

2. A pharmaceutical composition comprising a compound according to claim 1, in free or salt form.

* * * * *